United States Patent
Glucksmann et al.

(10) Patent No.: US 6,586,205 B1
(45) Date of Patent: Jul. 1, 2003

(54) 43239 A NOVEL GPCR-LIKE MOLECULE AND USES THEREOF

(75) Inventors: Maria Alexandra Glucksmann, Lexington, MA (US); Inmaculada Silos-Santiago, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/585,876

(22) Filed: Jun. 1, 2000

Related U.S. Application Data

(60) Provisional application No. 60/182,061, filed on Feb. 11, 2000.

(51) Int. Cl.$^7$ .............................. C12P 21/06; C12N 1/20; C12N 15/00; C07H 21/04
(52) U.S. Cl. ............... 435/69.1; 435/252.3; 435/320.1; 536/23.5
(58) Field of Search ....................... 536/23.5; 435/320.1, 435/325, 252.3, 69.1; 530/350

(56) References Cited

FOREIGN PATENT DOCUMENTS

| WO | WO 01/19986 A1 | 3/2001 |
|---|---|---|
| WO | WO 01/36471 A2 | 5/2001 |

OTHER PUBLICATIONS

Takasaki, et al, 2000, Biochem. Biophys. Res. Comm., 274: 316–322, esp. Fig. 4.*
Takasaki, 2000, Acc. No. NM_020377.*
Blaesius, R.H., 1998, Acc. No. Z94154.*
Skolnick, J. (2000) From genes to protein structure and function: novel applications of computational approaches in the genomic era. Trends in Biotech. 18(1):34–39.*
Bork, P. (2000) Powers and Pitfalls in Sequence Analysis: The 70% Hurdle. Genome Research 10:398–400.*
Doerks, T. et al (1998) Protein annotation: detective work for protein prediction. Trends in Genetics 14(6):248–250.*
Smith, T. et al, (1997) The challenges of genome sequence annotation or "The devil is in the details". Nature Biotech. 15:1222–1223.*
Ji, et al. 1998, J. Biol. Chem. 273(28):17299–17302, whole document.*
Brenner, S. (1999) Errors in genome annotation. Trends in Genetics 15(4):132–133.*
Bork, P. (1998) Go hunting in sequence databases but watch out for the traps. Trends in Genetics 12(10):425–427.*
Janssens, et al GenBank Accession No. AAB66322, May 26, 1997.
Lynch, et al GenBank Accession No. AAD42285, Jan. 12, 1999.
Blaesivs, et al GenBank Accession No. CAA73144, Apr. 14, 1997.
Blaesivs, et al GenBank Accession No. CAB08108, Apr. 16, 1997.
Kaplan, et al GenBank Accession No. P32250, Oct. 1, 1993.
Webb, et al GenBank Accession No. P34996, 1993.
Tokuyama, et al GenBank Accession No. P49651, 1995.
Filtz, et al GenBank Accession No. P49652, Feb. 1, 2996.
Raport, et al GenBank Accession No. Q13304, Nov. 1, 1997.
O'Dowd, et al GenBank Accession No. Q99677, 1997.
Dunn, M. GenBank Accession No. AL137118, Feb. 8, 2001.
GenBank Accession No. AL137118.
Heisee, C.E. et al., Characterization of the Human Cysteinyl Leukotriene 2 Receptor, *The Journal of Biological Chemistry*, Sep. 29, 2000, pp. 30531–30536, vol. 275, No. 39, The American Society for Biochemistry and Molecular Biology, Inc.
Abbracchio et al., "Purinergic Signalling: Pathophysiological Roles" (1998) *Jpn. J. Pharmacol.* 78:113–145.
Bläsius et al., "A Novel Orphan G Protein–Coupled Receptor Primarily Expressed in the Brain is Localized on Human Chromosomal Band 2q21" (1998) *J. Neurochem* 70:1357–1365.
Chen et al., "Ectopic Purinergic Sensitivity Develops at Sites of Chronic Nerve Constriction Injury in Rat" (1999) *NeuroReport* 10:2779–2782.
Filtz et al., "Expression of a Cloned $P_{2Y}$ Purinergic Receptor that Couples to Phospholipase C" (1994) *Molecular Pharmacology* 46:8–14.
Idestrup et al. "$P_{2Y}$ and $P_{2U}$ Receptors Differentially Release Intracellular $Ca^{2+}$ Via the Phospholipase C/Inositol 1,4, 5–Triphosphate Pathway in Astrocytes from the Dorsal Spinal Cord" (1998) *Neuroscience* 86(3):913–923.
Janssens et al., "Cloning of a Human Heptahelical Receptor Closely Related to the $P2Y_5$ Receptor" (1997) *Biochem. and Biophys. Res. Comm.* 236:106–112.
Kaplan et al., "Identification of a G Protein Coupled Receptor Induced in Activated T Cells" (1993) *J. Immunology* 151(2):628–636.

(List continued on next page.)

*Primary Examiner*—Lorraine Spector
*Assistant Examiner*—Sandra Wegert
(74) *Attorney, Agent, or Firm*—Millennium Pharmaceuticals, Inc.

(57) ABSTRACT

Novel GPCR-like polypeptides, proteins, and nucleic acid molecules are disclosed. In addition to isolated, full-length GPCR-like proteins, the invention further provides isolated GPCR-like fusion proteins, antigenic peptides, and anti-GPCR-like antibodies. The invention also provides GPCR-like nucleic acid molecules, recombinant expression vectors containing a nucleic acid molecule of the invention, host cells into which the expression vectors have been introduced, and nonhuman transgenic animals in which a GPCR-like gene has been introduced or disrupted. Diagnostic, screening, and therapeutic methods utilizing compositions of the invention are also provided.

8 Claims, 2 Drawing Sheets

OTHER PUBLICATIONS

Kunapuli et al., "$P_2$ Receptor Subtypes in the Cardiovascular System" (1998) *Biochem. J. 336*:513–523.

Li et al., "The 6H1 Orphan Receptor, Claimed to Be the p2y5 Receptor, Does Not Mediate Nucleotide–Promoted Second Messenger Responses" (1997) *Biochem. and Biophys. Res. Comm. 236*:455–460.

Lynch et al., "Characterization of the Human Cysteinyl Leukotriene $CysLT_1$ Receptor" (1999) *Nature 399*:789–793.

Mendoza–Fernandez et al., "ATP Inhibits Glutamate Synaptic Release by Acting at P2Y Receptors in Pyramidal Neurons of Hippocampal Slices" (2000) *JPET 293(1)*:172–179.

North et al., "Neucleotide Receptors" (1997) *Current Opinion in Neurobiology 7*:346–357.

O'Dowd et al., "Cloning and Chromosomal Mapping of Four Putative Novel Human G–Protein–Coupled Receptor Genes" (1997) *Gene 187*:75–81.

Pirotton et al., "Endothelial $P_2$–Purinoceptors: Subtypes and Signal Transduction" (1996)*J. Autonomic Pharmacology 16*:353–356.

Raport et al., "New Members of the Chemokine Receptor Gene Family" (1996)*J. Leukocyte Biol. 59*:18–23.

Tokuyama et al., "Cloning of Rat and Mouse $P_{2Y}$ Purinoceptors" (1995) *Biochem. and Biophys. Res. Comm. 211(1)*:211–218.

Van Rhee et al., "Modelling the $P_{2Y}$ Purinoceptor Using Rhodopsin as Template" (1995) *Drug Design and Discovery 13*:133–154.

Webb et al., "Cloning and Functional Expression of a Brain G–Protein–Coupled ATP Receptor" (1993) *FEBS 324(2)*:219–225.

Williams, "Developments in P2 Receptor Targeted Therapeutics" (1999) *Progress in Brain Research 120*:93–106.

* cited by examiner

43239 A NOVEL GPCR-LIKE MOLECULE AND USES THEREOF

CROSS-REFERENCE TO RELATED APPLICATION

This Application claims the benefit of U.S. Provisional Application No. 60/182,061, filed Feb. 11, 2000.

FIELD OF THE INVENTION

The invention relates to novel GPCR-like nucleic acid sequences and proteins. Also provided are vectors, host cells, and recombinant methods for making and using the novel molecules.

BACKGROUND OF THE INVENTION

G-protein coupled receptors (GPCRs) constitute a major class of proteins responsible for transducing a signal within a cell. GPCRs have three structural domains: an amino terminal extracellular domain, a transmembrane domain containing seven transmembrane segments, three extracellular loops, and three intracellular loops, and a carboxyl terminal intracellular domain. Upon binding of a ligand to an extracellular portion of a GPCR, a signal is transduced within the cell that results in a change in a biological or physiological property of the cell. GPCRs, along with G-proteins and effectors (intracellular enzymes and channels modulated by G-proteins), are the components of a modular signaling system that connects the state of intracellular second messengers to extracellular inputs.

GPCR genes and gene-products are potential causative agents of disease (Spiegel et al (1993), *J. Clin. Invest.* 92:1119–1125; McKusick et al., *J. Med. Genet.* (1993) 30:1–26). For example, specific defects in the rhodopsin gene and the V2 vasopressin receptor gene have been shown to cause various forms of retinitis pigmentosum (Nathans et al. (1992) *Annu. Rev. Genet.* 26:403–424), and nephrogenic diabetes insipidus (Holtzman et al. (1993) *Hum. Mol. Genet.* 2:1201–1204). These receptors are of critical importance to both the central nervous system and peripheral physiological processes. Evolutionary analyses suggest that the ancestor of these proteins originally developed in concert with complex body plans and nervous systems.

Metabotrophic (P2Y) receptors form a distinct subset of G-protein coupled receptors, whose ligands comprise adenosine 5'-triphosphate (ATP) and/or related nucleotides. P2Y receptors are generally distinguished pharmacologically by the rank order of effectiveness of agonists: some prefer pyrimidines to purines. More than eleven P2Y receptors have been reported. For a review see, for example, North et al. (1997) *Current Opinion in Neurobiology* 7:346–357. Presently, four subfamilies have been distinguished: 1) $P2Y_1$, 2) $P2Y_2/P2Y_4/P2Y_8$, 3) $P2Y_3/P2Y_6$, and, 4) $P2Y_5$. The P2 receptors may be coupled through G-proteins to signaling pathways involving phospholipase C (which increases inositol-1,4,5-trisphosphate and diacylglycerol formation), phospholipase A2 (with consequent generation of eicosanoids), or adenylate cyclase (which increases cAMP levels). Some members of this receptor family have also been shown to mediate their signals through the inhibition of adenylate cyclase, the inhibition of N-type $Ca^{2+}$ channels, and the activation of $K^+$ channels. For a review see Boarder et al. (1995) *Trends Pharmacol Sci* 16:133–139 and Neary et al. 1996 *Trends Neurosci* 19:13–18.

Endogenous ATP as well as the uracil congener, UTP, act as extracellular signaling molecules and mediate some of their effects via interactions through various members of the P2Y receptor family. Signal transduction through P2Y receptors has recently been implicated in the modulation of neuronal cell membrane ion channels. P2Y type receptors in the rat cerebella or hippocampal neurons (Ikeuchi et al. (1996) *Biochem Biophys Res Commun* 218:67–71) and guinea pig atrial cells (Matsuura et al. (1996) *J Physiol* 490:659–671) have been linked to the activation of $K^+$ channels. This coupling is G-protein mediated and membrane-delimited, thus adding P2Y receptors to the family of seven-transmembrane receptors known to act in this way. Furthermore, nucleotides inhibit endogenous $Ca^{2+}$ currents in neuroblastoma hybrid cells, which contain the $P2Y_2$ receptor. The direct involvement of $P2Y_2$ receptors in this cellular event has since been demonstrated through a direct approach. Rat sympathetic neurons have no native response to UTP. Microinjection of $P2Y_2$ receptor cRNA into the rat sympathetic neurons resulted in expression of the $P2Y_2$ receptor and an acquired UTP-mediated inhibition of their N-type $Ca^{2+}$ channels (Chen et al. (1996) *Endocrinology* 137:1833–1840 and Nicholas et al. (1996) *Mol Pharmacol* 50:224–229). Since $P2Y_2$ receptors are also known to activate phospholipase C, these results indicate that $P2Y_2$ receptors can mediate signal transduction through two independent pathways, depending on the cellular environment.

In $P2Y_1$-transfected COS-7 cells, agonists produce a transient increase in internal $Ca^{2+}$ associated with the formation of inositol-1,4,5-trisphosphate (Simon et al. (1995) *Eur J Pharmacol* 291:281–289). $P2Y_1$ receptors have been cloned from turkey brain, mouse and rat insulinoma cells, bovine aortic endothelia cells, rat brain, and human erythroid leukemia cells. Interestingly, the rat $P2Y_1$ receptors are expressed in endothelial cells (B10) isolated from the blood brain barrier. Various nucleotides have been found to mobilize $Ca^{2+}$ in these cells (Webb et al. (1996) *J Pharmacol* 119:1385–1392). However, the $Ca^{2+}$ mobilization response is associated not with an increase in inositol-1,4,5-trisphosphate but rather with the inhibition of adenylate cyclase. This is in contract to the signal transduction mediated by turkey (Filtz et al. (1994) *Mol Pharmacol* 46:8–14), chicken (Simon et al. (1995) *Pharmacol Toxicol* 76:302–307) or human (Schachter et al. (1 996) *Br J Phrmacol* 118:167–173) $P2Y_1$ receptors which when expressed heterologously, clearly induced only inositol-1,4,5-trisphosphate formation. Hence, the $P2Y_1$ receptor, while commonly coupled to phospholipase C, can in some native cells be coupled instead through the $G_0/G_i$ cyclase inhibitory pathway.

As extracellular signaling molecules, ATP and UTP are involved in various physiological and pathophysiological processes that have been associated with P2Y receptor family members. The role of ATP in tissue homeostasis, fast excitatory neurotransmission, tissue development, pain transmission, macrophage apoptosis, platelet aggregation, astroglia cell function, and the development and maturation of the nervous system has been established and current evidence indicates that the P2Y receptors mediate many of these cellular effects via an interaction with the extracellular ATP ligand. See for example, Burnstock et al. (1996) *Drug Dev. Res.* 39:204–242 and Williams et al (1999) *Progress in Brain Research* 120:93–106. Furthermore, UTP, acting via the P2Y receptors, is a potent and selective modulator of mucocilliary transport. Thus, members of the P2Y receptor family mediate cellular responses produced by extracellular ATP, UTP, and/or related nucleotides (Anderson et al. (1997) *Trends Pharmacol. Sci.* 18:387–392).

Extracellular ATP is known to be hyperalgesic: peripheral administration of ATP produces pain and ATP can enhance the production of prostaglandins that also produce pain (Needleman et al. (1974) *Circ. Res.* 34:455–460). Burnstock ((1996) *Autonomic Neuroscience Institute*, sheet 8) has suggested that locally produced ATP may contribute to the pain associated with causalgia, reflex sympathetic dystrophy, migraine, angina, lumbar, pelvic and cancer pain. Salter et al. have shown that P2Y receptors in dorsal horn astrocytes respond to ATP by increasing $Ca^{2+}$ levels and thus, P2Y receptors may be involved in mediating the pain response (Salter et al. (1994) *J. Neurosci.* 14:1563–1575). During reactive-hyperemia, large amounts of ATP are released from vascular endothelial cells that act on P2Y receptors, resulting in the release of nitric oxide and vasodilatation. Burnstock proposed that in the microcirculation, ATP diffuses from the endothelial cells to activate nociceptive endings of sensory nerve fibers in the adventitia (Burnstock (1996) *Lancet* 347:1604–1605). ATP released from platelets during aggregation, which has been reported to increase in migraine, may also contribute to the initiation of pain via nociceptive receptors. Consistent with this hypothesis is the finding that nociception from blood vessels is independent of the sympathetic nervous system under physiological conditions in humans (Kindgen et al. (1997) *Cur J. Pharmacol* 328:41–44).

Tumor cells are also known to contain exceptionally high levels of ATP. It has been suggested that when the tumor reaches a size that leads to breakage of cells during abrasive movements, the ATP released acts on nociceptive endings of sensory nerves in the vicinity, resulting in the sensation of pain. Furthermore, ATP released from damaged muscle following major accidents or surgery could be involved in local pain and in pain associated with traumatic shock. In addition to the hyperalgesic actions of ATP, the nucleotide has also been characterized as a messenger for innocuous mechanical stimuli and $P2Y_1$ receptors have been suggested to mediate tactile responses in sensory neurons.

Following pathological events in the brain tissue, purine nucleotides and nucleosides are released into the extracellular space. The (patho)physiological importance and molecular mechanisms of the purinoceptor-mediated effects are unknown. It has been suggested that following ischemic and other brain injuries, ATP play s a trophic role in the initiation and maintenance of reactive astrogliosis. Franke et al. (1999) *Glia* 28:190–200 found that the P2 antagonist, 2-MeSATP, stimulates gliosis following CNS injury. Specifically, the P2 antagonist reduced astroglial proliferation after stab wound as well as after application of 2-MeSATP. These results suggest the involvement of P2 receptors in the generation of astrogliosis in vivo.

The ability of high doses of ATP to evoke tonicclonic convulsions implicates the nucleotide in fast excitatory neurotransmission and thus, ATP may play a role in seizure generation (Buday et al. (1961) *J. Pharmacol* 8:2221–2228). Furthermore, ATP may be a prime mediator of neurogenic inflammation via its actions on P2 receptors on neutrophiles, macrophages and monocytes leading to cytokine and prostaglandin release (Dubyak et al. (1993) *Am. J. Physiol.* 265:C577–C606 and Needleman et al. (1974) *Circ. Res.* 34:455–460). In this context it is of interest that the putative $P2Y_7$ receptor cloned from human erythroleukemia cells was subsequently found to be the leukotriene B4 receptor, suggesting that the receptors for prostanoids and ATP may be functionally related.

Perilymphatic ATP, likely acting via P2Y receptors can depress the sound-evoked gross compound action potential of the auditory nerve and the distortion product otoacoustic emission, the latter a measure of the active process of the outer hair cells. (Kujawa et al. (1994) *Hear Res.* 76:87–100). P2Y receptor expression is also observed in the marginal cells of the stria vascularis, a tissue involved in providing the ionic and electrical gradients of the cochlea. Little is currently known about the pharmacology and receptor associated physiology of hearing and vestibular function, however, it has been suggested that ATP may regulate fluid homeostasis, hearing sensitivity, and development.

Furthermore, ATP and UTP are potent stimulants of chloride secretion in airway epithelium (Mason et al. (1993) *Am. Rev. Respir. Dis.* 147:A27) and mucin glycoprotein release from epithelial goblet cells (Lethem et al. (1993) *Am. J. Respir. Cell. Mol. Bio.* 9:315–322) acting via the $P2Y_2$ receptor. P2 receptors may therefore play a role in the ability of UTP to stimulate mucociliary clearance and sputum expectoration in smokers, non-smokers and patients with chronic bronchitis. ATP also appears to have a potential role in asthma and ATP and UTP have been demonstrated to potentiate IgE-mediated mast cell histamine release. Evidence indicates such effects-may be mediated by P2Y receptors (Schulman et al. (1998) *Drug Dev Res* 43:40).

Accordingly, GPCRs are a major target for drug action and development. Accordingly, it is valuable to the field of pharmaceutical development to identify and characterize previously unknown GPCRs. The present invention advances the state of the art by providing novel seven-transmembrane proteins/GPCRs.

SUMMARY OF THE INVENTION

Isolated nucleic acid molecules corresponding to GPCR-like nucleic acid sequences are provided. Additionally, amino acid sequences corresponding to the polynucleotides are encompassed. In particular, the present invention provides for isolated nucleic acid molecules comprising nucleotide sequences encoding the amino acid sequences shown in SEQ ID NO:2 or the nucleotide sequences encoding the DNA sequence deposited in a bacterial host as ATCC Accession Numbers PTA-2365, PTA-2166, and PTA-2366. Further provided are GPCR-like polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The GPCR-like molecules of the present invention are useful for modulating pain transmission; immune and inflammatory responses; cell growth, differentiation, and death; and, the release of hormones, neurotransmitters, and cytokines. The molecules are useful for the diagnosis and treatment of neurologic disorders, such as central nervous system or peripheral nervous system disorders, including, for example, epilepsy, schizophrenia, depression and anxiety, Alzheimer's and Parkinson's disease, trauma, ischemia, sclerosis, various forms of encephalopathies, and demyelinating diseases; pain disorders or conditions, including, for example, vascular pain, including angina, ischemic muscle pain, migraine, lumbar pain, pelvic pain, and sympathetic nerve activity including inflammation associated with arthritis; and exocrine and endocrine mediated disorders, including for example, disorders of airway electrolyte metabolism, i.e. cystic fibrosis, chronic airway infections, and other lung disorders. Disorders associated with the following cells or tissues are also encompassed:

brain, cortex, dorsal root ganglion (DRG) neurons, sciatic nerve, spinal cord, heart, kidney, gastro muscle, liver, lung, and, skin. Additionally, the molecules of the invention are useful as modulating agents in a variety of cellular processes including the mobilization of intracellular molecules that participate in a signal transduction pathway. Accordingly, in one aspect, this invention provides isolated nucleic acid molecules encoding GPCR-like proteins or biologically active portions thereof, as well as nucleic acid fragments suitable as primers or hybridization probes for the detection of GPCR-like-encoding nucleic acids.

Another aspect of this invention features isolated or recombinant GPCR-like proteins and polypeptides. Preferred GPCR-like proteins and polypeptides possess at least one biological activity possessed by naturally occurring GPCR-like proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

Antibodies and antibody fragments that selectively bind the GPCR-like polypeptides and fragments are provided. Such antibodies are useful in detecting the GPCR-like polypeptides as well as in regulating pain transmission, nervous system function and development, release of hormones, neurotransmitters and cytokines, immune and inflammatory responses and cell growth, differentiation and death.

In another aspect, the present invention provides a method for detecting the presence of GPCR-like activity or expression in a biological sample by contacting the biological sample with an agent capable of detecting an indicator of GPCR-like activity such that the presence of GPCR-like activity is detected in the biological sample.

In yet another aspect, the invention provides a method for modulating GPCR-like activity comprising contacting a cell with an agent that modulates (inhibits or stimulates) GPCR-like activity or expression such that GPCR-like activity or expression in the cell is modulated. In one embodiment, the agent is an antibody that specifically binds to GPCR-like protein. In another embodiment, the agent modulates expression of GPCR-like protein by modulating transcription of a GPCR-like gene, splicing of a GPCR-like mRNA, or translation of a GPCR-like mRNA. In yet another embodiment, the agent is a nucleic acid molecule having a nucleotide sequence that is antisense to the coding strand of the GPCR-like mRNA or the GPCR-like gene.

In one embodiment, the methods of the present invention are used to treat a subject having a disorder characterized by aberrant GPCR-like protein activity or nucleic acid expression by administering an agent that is a GPCR-like modulator to the subject. In one embodiment, the GPCR-like modulator is a GPCR-like protein. In another embodiment, the GPCR-like modulator is a GPCR-like nucleic acid molecule. In other embodiments, the GPCR-like modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding a GPCR-like protein; (2) misregulation of a gene encoding a GPCR-like protein; and (3) aberrant post-translational modification of a GPCR-like protein, wherein a wild-type form of the gene encodes a protein with a GPCR-like activity.

In another aspect, the invention provides a method for identifying a compound that binds to or modulates the activity of a GPCR-like protein. In general, such methods entail measuring a biological activity of a GPCR-like protein in the presence and absence of a test compound and identifying those compounds that alter the activity of the GPCR-like protein.

The invention also features methods for identifying a compound that modulates the expression of GPCR-like genes by measuring the expression of the GPCR-like sequences in the presence and absence of the compound.

Other features and advantages of the invention will be apparent from the following detailed description and claims.

DETAILED DESCRIPTION OF THE INVENTION

Figure 1:
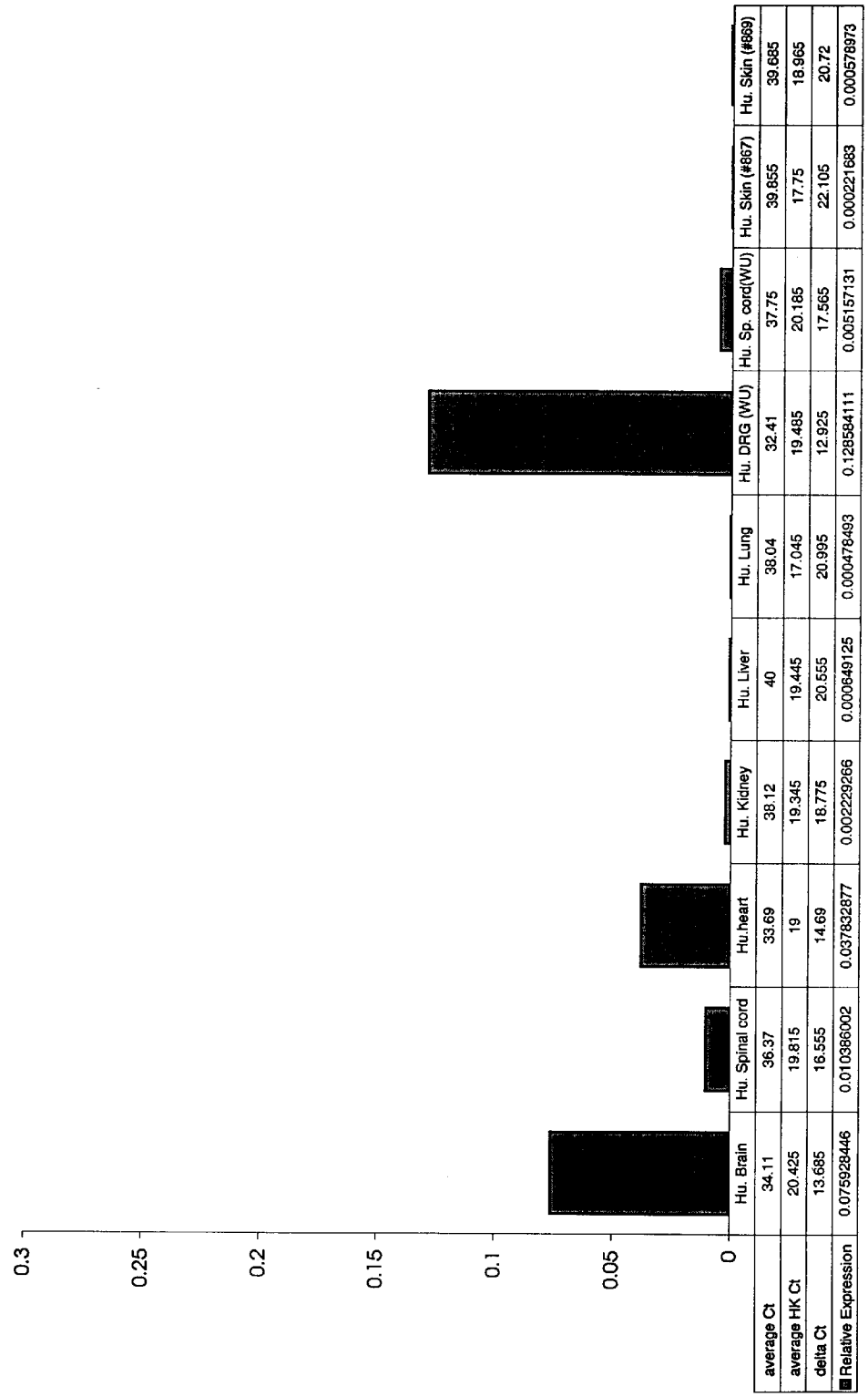
FIG. 1 shows expression of 43239 in various human tissues and cell types.

The present invention provides GPCR-like molecules. By "GPCR-like molecules" is intended a novel human sequence referred to as 43239, and variants and fragments thereof. These full-length gene sequences or fragments thereof are referred to as "GPCR-like" sequences, indicating they share sequence similarity with GPCR genes. Isolated nucleic acid molecules comprising nucleotide sequences encoding the 43239 polypeptide whose amino acid sequence is given in SEQ ID NO:2, or a variant or fragment thereof, are provided. A nucleotide sequence encoding the 43239 polypeptide is set forth in SEQ ID NO:1. The sequences are members of the G-protein coupled receptor family.

A novel human GPCR-like gene sequence, referred to as 43239, this gene sequence and variants and fragments thereof are encompassed by the term "GPCR-like" molecules or sequences as used herein. The GPCR-like sequences find use in modulating a GPCR-like function. By "modulating" is intended the upregulating or downregulating of a response. That is, the compositions of the invention affect the targeted activity in either a positive or negative fashion.

As used herein, a "signaling pathway" refers to the modulation (e.g., stimulation or inhibition) of a cellular function/activity upon the binding of a ligand to the receptor protein). The term "transmembrane segment" refers to a structural amino acid motif that includes a hydrophobic helix that spans the plasma membrane.

The response mediated by the receptor proteins depends on the type of cell. For example, in some cells, binding of a ligand to the receptor protein may stimulate an activity such as release of compounds, gating of a channel, cellular adhesion, migration, differentiation, etc., through phosphatidylinositol or cyclic AMP (cAMP) metabolism and turnover while in other cells, the binding of the ligand will produce a different result. As used herein, "phosphatidylinositol turnover and metabolism" refers to the molecules involved in the turnover and metabolism of phosphatidylinositol 4,5-bisphosphate ($PIP_2$) as well as to the activities of these molecules. $PIP_2$ is a phospholipid found in the cytosolic leaflet of the plasma membrane. Binding of ligand to the receptor activates, in some cells, the plasma-membrane enzyme phospholipase C that in turn can hydrolyze $PIP_2$ to produce 1,2-diacylglycerol (DAG) and inositol 1,4,5- triphosphate (IP$_3$). Once formed IP$_3$ can diffuse to the endoplasmic reticulum surface where it can bind an IP$_3$ receptor, e.g., a calcium channel protein containing an IP$_3$ binding site. IP$_3$ binding can induce opening of the channel, allowing calcium ions to be released into the cytoplasm. IP$_3$ can also be 1 5 phosphorylated by a specific kinase to form inositol 1 ,3,4,5-tetraphosphate (IP$_4$), a molecule which can cause calcium entry into the cytoplasm from the extracellular medium. IP$_3$ and IP$_4$ can subsequently be hydrolyzed very rapidly to the inactive products inositol 1,4-biphosphate (IP$_2$) and inositol 1,3,4-triphosphate, respectively. These inactive products can be recycled by the cell to synthesize PIP$_2$. The other second messenger produced by the hydrolysis of PIP$_2$, namely 1,2-diacylglycerol (DAG), remains in the cell membrane where it can serve to activate the enzyme protein kinase C. Protein kinase C is usually found soluble in the cytoplasm of the cell, but upon an increase in the intracellular calcium concentration, this enzyme can move to the plasma membrane where it can be activated by DAG. The activation of protein kinase C in different cells results in various cellular responses such as the phosphorylation of glycogen synthase, or the phosphorylation of various transcription factors, e.g., NF-kB. The language "phosphatidylinositol activity", as used herein, refers to an activity of PIP$_2$ or one of its metabolites.

Another signaling pathway in which the receptor may participate is the cAMP turnover pathway. As used herein, cAMP turnover and metabolism" refers to the molecules involved in the turnover and metabolism of cAMP as well as to the activities of these molecules. Cyclic AMP is a second messenger produced in response to ligand-induced stimulation of certain G protein coupled receptors. In the cAMP signaling pathway, binding of a ligand to a GPCR can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

Proteins and/or antibodies of the invention are also useful in modulating pain transmission, nervous system development and function, the release of hormones, neurotransmitters and cytokines, immune and inflammatory responses and cell growth, differentiation and death.

The disclosed invention relates to methods and compositions for the modulation, diagnosis, and treatment of neurologic disorders, such as central nervous system or peripheral nervous system disorders, including, for example, epilepsy, schizophrenia, pain, depression, anxiety, Alzheimer's disease, Parkinson's disease, trauma, ischemia, sclerosis, various forms of encephalopathies, and demyelinating diseases; pain disorders including, for example, vascular pain, including angina, ischemic muscle pain, migraine, lumbar pain, pelvic pain, and sympathetic nerve activity including inflammation associated with arthritis; and exocrine and endocrine mediated disorders, including, but not limited to, disorders of airway electrolyte metabolism, i.e. cystic fibrosis, chronic airway infections, and other lung disorders.

The invention also relates to disorders associated with tissues in which the sequences of the invention are expressed, including, for example, brain, cortex, dorsal root ganglion (DRG) neurons, sciatic nerve, spinal cord, heart, kidney, gastro muscle, liver, lung, and, skin. Disorders involving the brain include, but are not limited to, disorders involving neurons, and disorders involving glia; such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as. acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive mulItifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin B$_1$) deficiency and vitamin B$_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions; neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders of the peripheral nervous system include, inflammatory neuropathies, such as, immune-mediated neuropathies (i.e. Guillain-Barre syndrome); infectious polyneuropathies, such as, leprosy, diphtheria, varicella-zoster virus; hereditary neuropathies, such as, hereditary motor and sensory neuropathy I, HMSN II, Dejerine-Sottas Disease; acquired metabolic and toxic neuropathies, such as, peripheral neuropathy in adult-onset diabetes mellitus, metabolic and nutritional peripheral neuropathies, neuropathies associated with malignancy, toxic neuropathies; traumatic neuropathies; and tumors of the peripheral nerve.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, includinig but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypemephroma, adenocarcinoma of kidney), which includes urothelial carcinomas of renal pelvis.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus. erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

The GPCR-like gene, clone 43239 was identified in a human placenta cDNA library. Clone 43239 encodes an approximately 1.4 Kb mRNA transcript having the corresponding cDNA set forth in SEQ ID NO:1. This transcript has a 1040 nucleotide open reading frame (nucleotides 197–1237 of SEQ ID NO:1), which encodes a 346 amino acid protein (SEQ ID NO:2). An analysis of the full-length 43239 polypeptide predicts that the N-terminal 44 amino acids represent a signal peptide. Transmembrane segments from amino acids (aa) 24–48, 59–77, 106–125, 139–158, 187–209, 229–245, and 270–292 were predicted by MEMSAT. Transmembrane segments were also predicted from aa 16–34, 63–82, 96–115, 144–166, 186–202, and 227–249 of the presumed mature peptide sequence. Prosite program analysis was used to predict various sites within the 43239 protein. N-glycosylation sites were predicted at aa 4–7, 10–13, 14–17, and 165–168. A cAMP- and cGMP-dependent protein kinase phosphorylation sites were predicted at aa 52–55 and 325–328. Protein kinase C phosphorylation sites were predicted at aa 135–137, 225–227, 249–251, and 257–259. Casein kinase II phosphorylation sites were predicted at aa 160–163 and 170–173. N-myristoylation sites were predicted at aa 5–10, 36–41, 161–166, and 221–226. A prokaryotic membrane lipoprotein lipid attachment site was predicted at aa 184–194. The GPCR-like protein possesses a 7 transmembrane receptor domain of the rhodopsin-like GPCR superfamily from aa 39–289 as predicted by HMMer, Version 2. The rhodopsin-like GPCRs themselves represent a widespread protein family that includes hormones, neurotransmitters and light receptors, all of which transduce extracellular signals through interaction with guanine nueleotide-binding (G) proteins. See for example, Birnbaumer et al. (1990) *Annu. Rev. Pharmacol. Toxicol.* 30:675–705; Casey et al. (1988) *J. Biol. Chem.* 263:2577–2580; and Attwood et al. (1993) *Protein Eng.* 6:167–176.

The 43239 protein shares 38% identity to the human putative G-protein-coupled receptor GPR17P2Y-like G protein receptor (Genbank Acc. No. Q13304).

The 43239 protein displays 38% identity from aa 52–155 to a Prodom consensus sequence found in several proteins including: F57A8.4 protein from *Caenorhabditis elegans* (Genbank Acc. No. Q20915); G-protein coupled receptor 27 from *Mus musculus* (Genbank Acc. No. 054897); SRG-12 protein from *Caenorhabditis elegans* (Genbank Acc. No. P46564); C03G6.16 protein from *C. elegans* (Genbank Acc. No. 001459); GPR22 from *Homo sapiens* (Genbank Acc.

No. Q99680); G-protein coupled receptor GRL101 precursor from *Lymnaea stagnalis* (Genbank Acc. No. P46023); orphan G-protein-couple receptor HG38 from *Homo sapiens* (Genbank Acc. No. O75473); GPR31 from *Homo sapiens* (Genbank Acc. No. O00270); C39B10.1 protein from *C. elegans* (Genbank Acc. No. Q18517); RTA protein from *Rattus Norvegicus* (Genbank Acc. No. P23749); UL33 protein from human cytomegalovirus (Genbank Acc. No. P16849); and, ECRF3 protein from *Herpesvirus saimiri* (stain 11) (Genbank Acc. No. Q01035). GPR22 is an orphan receptor belonging to family 1 of the G-protein coupled receptors and is expressed in the brain in the frontal cortex, caudate, putamen, and thalamus. See, for example, O'Dowd et al. (1997) *Gene* 187:75–81. The GRL101 precursor belongs to family 1 of the G-protein couple receptors and is predominantly expressed in a small number of neurons within the central nervous system and to a lesser extent in the heart. See, for example, Tensen et al. (1994) *Proc. Nail. Acad Sci.* 91:4816–4820. RTA is also an orphan receptor belonging to family 1 of G-protein coupled receptors which is abundantly expressed in the cerebellum. See, for example, Ross et al. (1990) *Proc. Natl. Acad. Sci.* 87:3052–3056. ECRF3 is a member of the G-protein coupled receptor family 1. ECRF3 may be highly relevant to the process of cellular transformation and rapid T-cell proliferation effected by HVS during latent infections of T-cells in susceptible hosts. See, for example, Albrecht et al. (1992) *J. Virol.* 66:5047–5058.

The 43239 protein displays 23% identity from aa 191–309 to a Prodom consensus sequence found in several proteins that belong to family 1 of the G-protein coupled receptors including: protease-activated receptor 4 from *Homo sapiens* (Genbank Acc. No. O76067);PAR4 from *Mus musculus* (Genbank Acc. No. O88634). In addition, aa 183–299 display 26% identity to GPR25 from *Homo sapiens* (Genbank Acc. No. O00155) a family 1 G-protein coupled receptor.

The 43239 protein displays 44% identity from aa 1–57 to a Prodom consensus sequence found in the platelet activating factor receptor (PAR-R) from *Mus musculus* (Genbank Acc. No. Q62035), from *Homo sapiens* (Genbank Acc. No. P25105), from *Rattus norvegicus* (Genbank Acc. No. P46002), and from *Cavia porcellus* (Genbank Acc. No. P21556). PAR-R is a member of family 1 of the G-protein coupled receptors. PAR-R is a chemotactic phospholipid mediator that possesses potent inflammatory, smooth muscle contractile and hypotensive activity. See, for example, Ishii et al. (1996) *Biochem. J.* 314:671–678; Sugimoto et al. (1992) *Biochem. Biophys. Res. Commun.* 189:617–624; Bito et al. (1994) *Eur. J. Biochem.* 221:211–218; Honda et al. (1991) *Nature* 349:342–346.

The 43239 protein displays 26% identity from aa 74–205 to a Prodom consensus sequence found in several proteins having homology to members of family 2 of G-proteins including T13A10.7 from *C. elegans* (Cenbank Acc. No. Q22445); T13A10.8 from *C. elegans* (Genbank Acc. No. Q22446); T13A10.13 from *C. elegans* (Genbank Acc. No. Q22451); and T13A10.6 from *C. elegans* (Genbank Acc. No. Q22444). Furthermore, the 43239 protein displays 20% identity from aa 26–215 to a Prodom consensus sequence found in several proteins having homology to members of family 2 of the G-proteins including F49E11.2 from *C. elegans* (Genbank Acc. No. Q20601).

The 43239 protein displays 22% identity from aa 9–214 to a Prodom consensus sequence found in several protein including K06C4.9 from *C. elegans* (Genbank Acc. No. Q23004). And finally, the 43239 protein displays 26% identity from aa 34–156 to a Prodom consensus sequence found in several proteins including the hypothetical 41.1 KD protein from *Borrelia burgdorferi* (Genbank Acc. No. O51329).

Plasmids containing the 5'- and 3'-ends of the 43239 cDNA insert were deposited with the American Type Culture Collection (ATCC), 10801 University Boulevard, Manassas, Va., on Aug. 11, 2000, and assigned Accession Numbers PTA-2365 and PTA-2366, respectively. A plasmid containing the middle region of the 43239 cDNA insert was deposited with the American Type Culture Collection (ATCC), 10801 University Boulevard, Manassas, Va., on Jun. 27, 2000, and assigned Accession Number PTA-2166. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The GPCR-like sequences of the invention are members of a family of molecules (the "G-protein coupled receptor family") having conserved functional features. The term "family" when referring to the proteins and nucleic acid molecules of the invention is intended to mean two or more proteins or nucleic acid molecules having sufficient amino acid or nucleotide sequence identity as defined herein. Such family members can be naturally occurring and can be from either the same or different species. For example, a family can contain a first protein of murine origin and a homologue of that protein of human origin, as well as a second, distinct protein of human origin and a murine homologue of that protein. Members of a family may also have common functional characteristics.

Preferred GPCR-like polypeptides of the present invention have an amino acid sequence sufficiently identical to the amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 95%, or 98% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent-identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to GPCR-like nucleic acid molecules of the invention. BLAST protein searches can be performed with the XBLAST program, score=50, wordlength=3, to obtain amino acid sequences homologous to GPCR-like protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See World Wide Web Site ncbi.nlm.nih.gov. Another preferred, non-limiting example of a mathematical algorithm utilized for the comparison of sequences is the algorithm of Myers and Miller (1988) *CABIOS* 4:11–17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Accordingly, another embodiment of the invention features isolated GPCR-like proteins and polypeptides having a GPCR-like protein activity. As used interchangeably herein, a "GPCR-like protein activity", "biological activity of a GPCR-like protein", or "functional activity of a GPCR-like protein" refers to an activity exerted by a GPCR-like protein, polypeptide, or nucleic acid molecule on a GPCR-like responsive cell as determined in vivo, or in vitro, according to standard assay techniques. A GPCR-like activity can be a direct activity, such as an association with or an enzymatic activity on a second protein, or an indirect activity, such as a cellular signaling activity mediated by interaction of the GPCR-like protein with a second protein. In a preferred embodiment, a GPCR-like activity includes at least one or more of the following activities: (1) modulating (stimulating and/or enhancing or inhibiting) exocrine and endocrine secretions, for example, influence hormone release (i.e. insulin), ion absorption and secretion, and gastric acid secretion (2) modulating immune cell function, for example, influence cytokine maturation and natural killer cell activity, induce specialized cell functions such as migration, secretion and phagocytosis, and influence the regulation of immune cell activation in cancer and autoimmune diseases, (3) modulating cell proliferation and growth, for example, influence DNA synthesis or mitosis, (4) modulating nervous system (central and peripheral) development, function and etiopathology, for example, influence astroglia and microglia cell proliferation and formation of reactive astrocytes, influence brain repair following trauma and ischemia, influence purinergic transmission (both nerve-nerve and nerve-muscle), influence astrogliosis, influence ion channels, and regulate neuritogenesis, (5) modulating tumor growth and apoptosis, (6) modulating inflammation, for example, influence activation of sensory fibers and pain generation, influence signals for macrophage activation and neutrophil infiltration in the inflammatory area, stimulate inflammatory mediators such as arachidonate-derived inflammatory mediators, influence the release of lysosomal enzymes and the upregulation of lymphocyte adherence, and influence maturation and differentiation of immune cells, (7) modulating pain transmission, for example, stimulate sensory nerve endings and increase the discharge from sensory neurons, and (8) modulating the mobilization of intracellular molecules that participate in a signal transduction pathway, e.g., phosphatidylinositol 4,5-bisphosphate ($PIP_2$), inositol 1,4,5-triphosphate ($IP_3$) and adenylate cyclase.

An "isolated" or "purified" GPCR-like nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated GPCR-like nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A GPCR-like protein that is substantially free of cellular material includes preparations of GPCR-like protein having less than about 30%, 20%, 10%, or 5% (by dry weight) of non-GPCR-like protein (also referred to herein as a "contaminating protein"). When the GPCR-like protein or biologically active portion thereof is recombinantly produced, preferably, culture medium represents less than about 30%, 20%, 10%, or 5% of the volume of the protein preparation. When GPCR-like protein is produced by chemical synthesis, preferably the protein preparations have less than about 30%, 20%, 10%, or 5% (by dry weight) of chemical precursors or non-GPCR-like chemicals.

Various aspects of the invention are described in further detail in the following subsections.

I. Isolated Nucleic Acid Molecules

One aspect of the invention pertains to isolated nucleic acid molecules comprising nucleotide sequences encoding GPCR-like proteins and polypeptides or biologically active portions thereof, as well as nucleic acid molecules sufficient for use as hybridization probes to identify GPCR-like-encoding nucleic acids (e.g., GPCR-like mRNA) and fragments for use as PCR primers for the amplification or mutation of GPCR-like nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the GPCR-like proteins of the present invention include sequences set forth in SEQ ID NO:1, the nucleotide sequence of the cDNA insert of the plasmids deposited with the ATCC as Accession Numbers PTA-2365, PTA-2166, and PTA-2366 (the "cDNA of ATCC PTA-2365, PTA-2166, and PTA-2366"), and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the GPCR-like protein encoded by these nucleotide sequences is set forth in SEQ ID NO:2. The invention also encompasses nucleic acid molecules comprising nucleotide sequences encoding partial-length GPCR-like proteins, including the sequence set forth in SEQ ID NO:1, and complements thereof.

Nucleic acid molecules that are fragments of these GPCR-like nucleotide sequences are also encompassed by the present invention. By "fragment" is intended a portion of the nucleotide sequence encoding a GPCR-like protein. A fragment of a GPCR-like nucleotide sequence may encode a biologically active portion of a GPCR-like protein, or it may be a fragment that can be used as a hybridization probe or PCR primer using methods disclosed below. A biologically active portion of a GPCR-like protein can be prepared by isolating a portion of one of the 43239 nucleotide sequences of the invention, expressing the encoded portion of the GPCR-like protein (e.g., by recombinant expression in vitro), and assessing the activity of the encoded portion of the GPCR-like protein. Nucleic acid molecules that are fragments of a GPCR-like nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400 nucleotides, or up to the number of nucleotides present in a full-length GPCR-like nucleotide sequence disclosed herein (for example, 1401 nucleotides for SEQ ID NO:1) depending upon the intended use.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of a GPCR-like nucleotide sequence that encodes a biologically active portion of a GPCR-like protein of the invention will encode at least about 15, 25, 30, 50, 75, 100, 125, 150, 175, 200, 250, or 300 contiguous amino acids, or up to the total number of amino acids present in a full-length GPCR-like protein of the invention (for example, 346 amino acids for SEQ ID NO:2). Fragments of a GPCR-like nucleotide sequence that are useful as hybridization probes for PCR primers generally need not encode a biologically active portion of a GPCR-like protein.

Nucleic acid molecules that are variants of the GPCR-like nucleotide sequences disclosed herein are also encompassed by the present invention. "Variants" of the GPCR-like nucleotide sequences include those sequences that encode the GPCR-like proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the GPCR-like proteins disclosed in the present invention as discussed below. Generally, nucleotide sequence variants of the invention will have at least about 45%, 55%, 65%, 75%, 85%, 95%, or 98% identity to a particular nucleotide sequence disclosed herein. A variant GPCR-like nucleotide sequence will encode a GPCR-like protein that has an amino acid sequence having at least about 45%, 55%, 65%, 75%, 85%, 95%, or 98% identity to the amino acid sequence of a GPCR-like protein disclosed herein.

In addition to the GPCR-like nucleotide sequences shown in SEQ ID NOs:1 and 3, and the nucleotide sequence of the cDNA of ATCC PTA-2365, PTA-2166, and PTA-2366, it will be appreciated by those skilled in the art that DNA sequence polymorphisms that lead to changes in the amino acid sequences of GPCR-like proteins may exist within a population (e.g., the human population). Such genetic polymorphism in a GPCR-like gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a GPCR-like protein, preferably a mammalia GPCR-like protein. As used herein, the phrase "allelic variant" refers to a nucleotide sequence that occurs at a GPCR-like locus or to a polypeptide encoded by the nucleotide sequence. Such natural allelic variations can typically result in 1–5% variance in the nucleotide sequence of the GPCR-like gene. Any and all such nucleotide variations and resulting amino acid polymorphisms or variations in a GPCR-like sequence that are the result of natural allelic variation and that do not alter the functional activity of GPCR-like proteins are intended to be within the scope of the invention.

Moreover, nucleic acid molecules encoding GPCR-like proteins from other species (GPCR-like homologues), which have a nucleotide sequence differing from that of the GPCR-like sequences disclosed herein, are intended to be within the scope of the invention. For example, nucleic acid molecules corresponding to natural allelic variants and homologues of the human GPCR-like cDNA of the invention can be isolated based on their identity to the human GPCR-like nucleic acid disclosed herein using the human cDNA, or a portion thereof, as a hybridization probe according to standard hybridization techniques under stringent hybridization conditions as disclosed below.

In addition to naturally-occurring allelic variants of the GPCR-like sequences that may exist in the population, the skilled artisan will further appreciate that changes can be introduced by mutation into the nucleotide sequences of the invention thereby leading to changes in the amino acid sequence of the encoded GPCR-like proteins, without altering the biological activity of the GPCR-like proteins. Thus, an isolated nucleic acid molecule encoding a GPCR-like protein having a sequence that differs from that of SEQ ID NO:2 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated miutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a GPCR-like protein (e.g., the sequence of SEQ ID NO:2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif.

Alternatively, variant GPCR-like nucleotide sequences can be made by introducing mutations randomly along all or part of a GPCR-like coding sequence, such as by saturation mutagenesis, and the resultant mutants can be screened for GPCR-like biological activity to identify mutants that retain activity. Following mutagenesis, the encoded protein can be expressed recombinantly, and the activity of the protein can be determined using standard assay-techniques.

Thus the nucleotide sequences of the invention include the sequences disclosed herein as well as fragments and variants thereof. The GPCR-like nucleotide sequences of the invention, and fragments and variants thereof, can be used as probes and/or primers to identify and/or clone GPCR-like homologues in other cell types, e.g., from other tissues, as well as GPCR-like homologues from other mammals. Such probes can be used to detect transcripts or genomic sequences encoding the same or identical proteins. These probes can be used as part of a diagnostic test kit for identifying cells or tissues that misexpress a GPCR-like protein, such as by measuring levels of a GPCR-like-encoding nucleic acid in a sample of cells from a subject, e.g., detecting GPCR-like mRNA levels or determining whether a genomic GPCR-like gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). GPCR-like nucleotide sequences isolated based on their sequence identity to the GPCR-like nucleotide sequences set forth herein or to fragments and variants thereof are encompassed by the present invention.

In a hybridization method, all or part of a known GPCR-like nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known GPCR-like nucleotide sequence disclosed herein. Degenerate primers designed on the basis of conserved nucleotides or amino acid residues in a known GPCR-like nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a GPCR-like nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified GPCR-like nucleic acid molecule hybridizes under stringent conditions to a probe that is a nucleic acid molecule comprising one of the GPCR-like nucleotide sequences of the invention or a fragment thereof. In another embodiment, the previously unknown GPCR-like nucleic acid molecule is at least about 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising one of the GPCR-like nucleotide sequences disclosed herein or a fragment thereof.

Accordingly, in another embodiment, an isolated previously unknown GPCR-li e nuleic acid molecule of the invention is at least about 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising one of the nucleotide sequences of the invention, preferably the coding sequence set forth in SEQ ID NO:1, the cDNA of ATCC PTA-2365, PTA-2166, and PTA-2366, or a complement, fragment, or variant thereof.

As used herein, the term "hybridizes under stringent conditions" is intended to describe conditions for hybridization and washing under which nucleotide sequences having at least about 60%, 65%, 70%, preferably 75% identity to each other typically remain hybridized to each other. Such stringent conditions are known to those skilled in the art and can be found in *Current Protocols in Molecular Biology* (John Wiley & Sons, New York (1989)), 6.3.1–6.3.6. A preferred, non-limiting example of stringent hybridization conditions is hybridization in 6×sodium chloride/sodium citrate (SSC) at about 45° C., followed by one or more washes in 0.2×SSC, 0.1% SDS at 50–65° C. In another preferred embodiment, stringent conditions comprise hybridization in 6×SSC at 42° C., followed by washing with 1×SSC at 55° C. Preferably, an isolated nucleic acid molecule that hybridizes under stringent conditions to a GPCR-like sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Thus, in addition to the GPCR-like nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the GPCR-like nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire GPCR-like coding strand, or to only a portion thereof, e.g., all or part of the protein coding region (or open reading frame). An antisense nucleic acid molecule can be antisense to a noncoding region of the coding strand of a nucleotide sequence encoding a GPCR-like protein. The noncoding regions are the 5' and 3' sequences that flank the coding region and are not translated into amino acids.

Given the coding-strand sequence encoding a GPCR-like protein disclosed herein (e.g., SEQ ID NO:1), antisense nucleic acids of the invention can be designed according to the rules of Watson and Crick base pairing. The antisense nucleic acid molecule can be complementary to the entire coding region of GPCR-like mRNA, but more preferably is an oligonucleotide that is antisense to only a portion of the coding or noncoding region of GPCR-like mRNA. For example, the antisense oligonucleotide can be complementary to the region surrounding the translation start site of GPCR-like mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

When used therapeutically, the antisense nucleic acid molecules of the invention are typically administered to a subject or generated in situ such that they hybridize with or bind to cellular mRNA and/or genomic DNA encoding a GPCR-like protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) Nature 334:585–591)) can be used to catalytically cleave GPCR-like mRNA transcripts to thereby inhibit translation of GPCR-like mRNA. A ribozyme having specificity for a GPCR-like-encoding nucleic acid can be designed based upon the nucleotide sequence of a GPCR-like cDNA disclosed herein (e.g., SEQ ID NO:1). See, e.g., Cech et al., U.S. Pat. No. 4,987,071; and Cech et al., U.S. Pat. No. 5,116,742. Alternatively, GPCR-like mRNA can be used to select a catalytic RNA having a specific ribonuclease activity from a pool of RNA molecules. See, e.g., Bartel and Szostak (1993) Science 261:1411–1418.

The invention also encompasses nucleic acid molecules that form triple helical structures. For example, GPCR-like gene expression can be inhibited by targeting nucleotide sequences complementary to the regulatory region of the GPCR-like protein (e.g., the GPCR-like promoter and/or enhancers) to form triple helical structures that prevent transcription of the GPCR-like gene in target cells. See generally Helene (1991) Anticancer Drug Des. 6(6):569; Helene (1992) Ann. N.Y. Acad. Sci. 660:27; and Maher (1992) Bioassays 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described, for example, in Hyrup et al. (1996), supra; Perry-O'Keefe et al. (1996) Proc. Natl. Acad. Sci. USA 93:14670.

PNAs of a GPCR-like molecule can be used in therapeutic and-diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), Suapra); or as probes or primers for DNA sequence and hybridization (Hyrup (1996), supra; Perry-O'Keefe et al. (1996), supra).

In another embodiment, PNAs of a GPCR-like molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) Nucleic Acids Res. 24(17):3357–63; Mag et al. (1989) Nucleic Acids Res. 17:5973; and Peterson et al. (1975) Bioorganic Med. Chem. Lett. 5:1119.

II. Isolated GPCR-like Proteins and Anti-GPCR-like Antibodies

GPCR-like proteins are also encompassed within the present invention. By "GPCR-like protein" is intended a protein having the amino acid sequence set forth in SEQ ID NO:2, as well as fragments, biologically active portions, and variants thereof.

"Fragments" or "biologically active portions" include polypeptide fragments suitable for use as immunogens to raise anti-GPCR-like antibodies. Fragments include peptides comprising amino acid sequences sufficiently identical to or derived from the amino acid sequence of a GPCR-like protein, or partial-length protein, of the invention and exhibiting at least-one activity of a GPCR-like protein, but which include fewer amino acids than the full-length,(SEQ ID NO:2). GPCR-like protein disclosed herein. Typically, biologically active portions comprise a domain or motif with at least one activity of the GPCR-like protein. A biologically active portion of a GPCR-like protein can be a polypeptide which is, for example, 10, 25, 50, 100 or more amino acids in length. Such biologically active portions can be prepared by recombinant techniques and evaluated for one or more of the functional activities of a native GPCR-like protein. As used here, a fragment comprises at least 5 contiguous amino acids of SEQ ID NO:2. The invention encompasses other fragments, however, such as any fragment in the protein greater than 6, 7, 8, or 9 amino acids.

By "variants" is intended proteins or polypeptides having an amino acid sequence that is at least about 45%, 55%, 65%, preferably about 75%, 85%, 95%, or 98% identical to the amino acid sequence of SEQ ID NO:2. Variants also include polypeptides encoded by the cDNA insert of the plasmids deposited with the ATCC as Accession Numbers PTA-2365, PTA-2166, and PTA-2366, or polypeptides encoded by a nucleic acid molecule that hybridizes to the nucleic acid molecule of SEQ ID NO:1, or a complement thereof, under stringent conditions. Such variants generally retain the functional activity of the GPCR-like proteins of the invention. Variants include polypeptides that differ in amino acid sequence due to natural allelic variation or mutagenesis.

The invention alsoprovides GPCR-like chimeric or fusion proteins. As used herein, a GPCR-like "chimeric protein" or "fusion protein" comprises a GPCR-like polypeptide operably linked to a non-GPCR-like polypeptide. A "GPCR-like polypeptide" refers to a polypeptide having an amino acid sequence corresponding to a GPCR-like protein, whereas a "non-GPCR-like polypeptide" refers to a polypeptide having an amino acid sequence corresponding to a protein that is not substantially identical to the GPCR-like protein, e.g., a protein that is different from the GPCR-like protein and which is derived from the same or a different organism. Within a GPCR-like fusion protein, the GPCR-like polypeptide can correspond to all or a portion of a GPCR-like protein, preferably at least one biologically active portion of a GPCR-like protein. Within the fusion protein, the term "operably linked" is intended to indicate that the GPCR-like polypeptide and the non-GPCR-like polypeptide are fused in-frame to each other. The non-GPCR-like polypeptide can be fused to the N-terminus or C-terminus of the GPCR-like polypeptide.

One useful fusion protein is a GST-GPCR-like fusion protein in which the GPCR-like sequences are fused to the C-terminus of the GST sequences. Such fusion proteins can facilitate the purification of recombinant GPCR-like proteins.

In yet another embodiment, the fusion protein is a GPCR-like-immunoglobulin fusion protein in which all or part of a GPCR-like protein is fused to sequences derived from a member of the immunoglobulin protein family. The GPCR-like-immunoglobulin fusion proteins of the invention can be incorporated into pharmaceutical compositions and administered to a subject to inhibit an interaction between a GPCR-like ligand and a GPCR-like protein on the surface of a cell, thereby suppressing GPCR-like-mediated signal transduction in vivo. The GPCR-like-immunoglobulin fusion proteins can be used to affect the bioavailability of a GPCR-like cognate ligand. Inhibition of the GPCR-like ligand/GPCR-like interaction may be useful therapeutically, both for treating pain, central and peripheral nervous system disorders and for modulating (e.g., promoting or inhibiting pain transmission, release of hormones, neurotransmitters, and cytokines, immune and inflammatory responses and cell growth, differentiation and death. Moreover, the GPCR-like -immunoglobulin fusion proteins of the invention can be used as immunogens to produce anti-GPCR-like antibodies in a subject, to purify GPCR-like ligands, and in screening assays to identify molecules that inhibit the interaction of a GPCR-like protein with a GPCR-like ligand.

Preferably, a GPCR-like chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a GPCR-like-encoding nucleic acid can be cloned into a commercially available expression vector such that it is linked in-frame to an existing fusion moiety.

Variants of the GPCR-like proteins can function as either GPCR-like agonists (mimetics) or as GPCR-like antagonists. Variants of the GPCR-like protein can be generated by mutagenesis, e.g., discrete point mutation or truncation of the GPCR-like protein. An agonist of the GPCR-like protein can retain substantially the same, or a subset, of the biological activities of the naturally occurring form of the GPCR-like protein. An antagonist of the GPCR-like protein can inhibit one or more of the activities of the naturally occurring form of the GPCR-like protein by, for example, competitively binding to a downstream or upstream member of a cellular signaling cascade that includes the GPCR-like protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the GPCR-like proteins.

Variants of a GPCR-like protein that function as either GPCR-like agonists or as GPCR-like antagonists can be identified by screening combinatorial libraries of mutants, e.g., truncation mutants, of a GPCR-like protein for GPCR-like protein agonist or antagonist activity. In one embodiment, a variegated library of GPCR-like variants is generated by combinatorial mutagenesis at the nucleic acid level and is encoded by a variegated gene library. A variegated library of GPCR-like variants can be produced by, for example, enzymatically ligating a mixture of synthetic oligonucleotides into gene sequences such that a degenerate set of potential GPCR-like sequences is expressible as individual polypeptides, or alternatively, as a set of larger fusion proteins (e.g., for phage display) containing the set of GPCR-like sequences therein. There are a variety of methods that can be used to produce libraries of potential GPCR-like variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential GPCR-like sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a GPCR-like protein coding sequence can be used to generate a variegated population of GPCR-like fragments for screening and subsequent selection of variants of a GPCR-like protein. In one embodiment, a library of coding sequence fragments can be generated by treating a double-stranded PCR fragment of a GPCR-like coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the GPCR-like protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of GPCR-like proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify GPCR-like variants (Arkin and Yourvan (1992) *Proc. Natl. Acad. Sci. USA* 89:7811–7815; Delgrave et al. (1993) *Protein Engineering* 6(3):327–331).

An isolated GPCR-like polypeptide of the invention can be used as an immunogen to generate antibodies that bind GPCR-like proteins using standard techniques for polyclonal and monoclonal antibody preparation. The full-length GPCR-like protein can be used or, alternatively, the invention provides antigenic peptide fragments of GPCR-like proteins for use as immunogens. The antigenic peptide of a GPCR-like protein comprises at least 8, preferably 10, 15, 20, or 30 amino acid residues of the amino acid sequence shown in SEQ ID NO:2 and encompasses an epitope of a GPCR-like protein such that an antibody raised against the peptide forms a specific immune complex with the GPCR-like protein. Preferred epitopes encompassed by the antigenic peptide are regions of a GPCR-like protein that are located on the surface of the protein, e.g., hydrophilic regions.

Accordingly, another aspect of the invention pertains to anti-GPCR-like polyclonal and monoclonal antibodies that bind a GPCR-like protein. Polyclonal anti-GPCR-like antibodies can be prepared by immunizing a suitable subject (e.g., rabbit, goat, mouse, or other mammal) with a GPCR-like immunogen. The anti-GPCR-like antibody titer in the immunized subject can be monitored over time by standard techniques, such as with an enzyme linked immunosorbent assay (ELISA) using immobilized GPCR-like protein. At an appropriate time after immunization, e.g., when the anti-GPCR-like antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1 994) *Current Protocols in Immunology* (John Wiley & Sons, Inc., New York, N.Y.); Galfre et al. (1 977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-GPCR-like antibody can be identified and isolated by screening a recombinant combinatorial immunoglobulin library (e.g., an antibody phage display library) with a GPCR-like protein to thereby isolate immunoglobulin library members that bind the GPCR-like protein. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod, Hybridomas* 3:81–85; Huse et al. (1989) *Science* 246:1275–1281; Griffiths et al. (1993) *EMBO J*. 12:725–734.

Additionally, recombinant anti-GPCR-like antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86/101533 and WO 87/02671; European Patent Application Nos. 184,187, 171,496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-GPCR-like antibody (e.g., monoclonal antibody) can be used to isolate GPCR-like proteins by standard techrniques, such as affinity chromatography or immunoprecipitation. An anti-GPCR-like antibody can facilitate the purification of natural GPCR-like protein from cells and of recombinantly produced GPCR-like protein expressed in host cells. Moreover, an anti-GPCR-like antibody can be used to detect GPCR-like protein (e.g., in a cellular lysate or cell supernatant) in order to evaluate the abundance and pattern of expression of the GPCR-like protein. Anti-GPCR-like antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emnetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procairie, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding a GPCR-like protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adenoassociated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., GPCR-like proteins, mutant forms of GPCR-like proteins, fusion proteins, etc.).

The recombinant expression vectors of the invention can be designed for expression of GPCR-like protein in prokaryotic or eukaryotic host cells. Expression of proteins in prokaryotes is most often carried out in *E. coli* with vectors containing constitutive or inducible promoters directing the expression of either fuision or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann el al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, CA), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cereivisiae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (e.g., liver-specific promoter; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Patent Publication No. 264,166). Developmentally-regulated promoters are also encompassed, for example the murine hox homeobox promoters (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to GPCR-like mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of artrecognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding a GPCR-like protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) GPCR-like protein. Accordingly, the invention further provides methods for producing GPCR-like protein using the host cells of the invention. In one embodiment, the method comprises culturing the host cell of the invention, into which a recombinant expression vector encoding a GPCR-like protein has been introduced, in a suitable medium such that GPCR-like protein is produced. In another embodiment, the method further comprises isolating GPCR-like protein from the medium or the host cell.

The host cells of the invention can also be used to produce nonhuman transgenic animals. For example, in one embodiment, a host cell of the invention is a fertilized oocyte or an embryonic stem cell into which GPCR-like-coding sequences have been introduced. Such host cells can then be used to create nonhuman transgenic animals in which exogenous GPCR-like sequences have been introduced into their genome or homologous recombinant animals in which endogenous GPCR-like sequences have been altered. Such animals are useful for studying the function and/or activity of GPCR-like genes and proteins and for identifying and/or evaluating modulators of GPCR-like activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous GPCR-like gene has been altered by homologous recombination between the endogenous gene and an exogenous DNA molecule introduced into a cell of the animal, e.g., an embryonic cell of the animal, prior to development of the animal.

A transgenic animal of the invention can be created by introducing GPCR-like-encoding nucleic acid into the male pronuclei of a fertilized oocyte, e.g., by microinjection, retroviral infection, and allowing the oocyte to develop in a pseudopregnant female foster animal. The GPCR-like cDNA sequence can be introduced as a transgene into the genome of a nonhuman animal. Alternatively, a homologue of the mouse GPCR-like gene can be isolated based on hybridization and used as a transgene. Intronic sequences and polyadenylation signals can also be included in the transgene to increase the efficiency of expression of the transgene. A tissue-specific regulatory sequence(s) can be operably linked to the GPCR-like transgene to direct expression of GPCR-like protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873, 191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the GPCR-like transgene in its genome and/or expression of GPCR-like mRNA in tissues or cells of the animals. A transgenic founder animal can then be used to breed additional animals carrying the transgene. Moreover, transgenic animals carrying a transgene encoding GPCR-like gene can further be bred to other transgenic animals carrying other transgenes.

To create a homologous recombinant animal, one prepares a vector containing at least a portion of a GPCR-like gene or a homolog of the gene into which a deletion, addition, or substitution has been introduced to thereby alter, e.g., functionally disrupt, the GPCR-like gene. In a preferred embodiment, the vector is designed such that, upon homologous recombination, the endogenous GPCR-like gene is functionally disrupted (i.e., no longer encodes a functional protein; also referred to as a "knock out" vector). Alternatively, the vector can be designed such that, upon homologous recombination, the endogenous GPCR-like gene is mutated or otherwise altered but still encodes functional protein (e.g., the upstream regulatory region can be altered to thereby alter the expression of the endogenous GPCR-like protein). In the homologous recombination vector, the altered portion of the GPCR-like gene is flanked at its 5' and 3' ends by additional nucleic acid of the GPCR-like gene to allow for homologous recombination to occur between the exogenous GPCR-like gene carried by the vector and an endogenous GPCR-like gene in an embryonic stem cell. The additional flanking GPCR-likenucleic acid is of sufficient length for successful homologous recombination with the endogenous gene. Typically, several kilobases of flanking DNA (at both the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced GPCR-like gene has homologously recombined with the endogenous GPCR-like gene are selected (see, e.g., Li et al. (1 992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating-two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810–813 and PCT Publication Nos. WO 97/07668 and WO 97/07669.

IV. Pharmaceutical Compositions

The GPCR-like nucleic acid molecules, GPCR-like proteins, and anti-GPCR-like antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the knowledge of the ordinarily skilled physician, veterinarian; or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a GPCR-like protein or anti-GPCR-like antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected -cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 $\mu$g/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 $\mu$g/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express GPCR-like protein (e.g., via a recombinant expression vector in a host cell in gene therapy applications), to detect GPCR-like mRNA (e.g., in a biological sample) or a genetic lesion in a GPCR-like gene, and to modulate GPCR-like activity. In addition, the GPCR-like proteins can be used to screen drugs or compounds that modulate pain transmission, immune and inflammatory responses, and nervous system function and development as well as to treat disorders characterized by insufficient or excessive production of GPCR-like protein or production of GPCR-like protein forms that have decreased or aberrant activity compared to GPCR-like wild type protein. In addition, the anti-GPCR-like antibodies of the invention can be used to detect and isolate GPCR-like proteins and modulate GPCR-like activity.

A. Screening Assays

The invention provides a method (also referred to herein as a "screening assay") for identifying modulators, i.e., candidate or test compounds or agents (e.g., peptides, peptidomimetics, small molecules, or other drugs) that bind-to GPCR-like proteins or have a stimulatory or inhibitory effect on, for example, GPCR-like expression or GPCR-like activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med, Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *BioTechniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223, 409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the GPCR-like protein can be accomplished, for example, by coupling the test compound with a radioisotope or enzymatic label such that binding of the test compound to the GPCR-like protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the GPCR-like protein to bind to or interact with a GPCR-like target molecule. By "target molecule" is intended a molecule with which a GPCR-like protein binds or interacts in nature. In a preferred embodiment, the ability of the GPCR-like protein to bind to or interact with a GPCR-like target molecule can be determined by monitoring the activity of the target molecule. For example, the activity of the target molecule can be monitored by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a GPCR-like-responsive regulatory element operably linked to a nucleic acid encoding a detectable marker, e.g. luciferase), or detecting a cellular response, for example, cellular differentiation or cell proliferation.

In yet another embodiment, an assay of the present invention is a cell-free assay comprising contacting a GPCR-like protein or biologically active portion thereof with a test compound and determining the ability of the test compound to bind to the GPCR-like protein or biologically active portion thereof. Binding of the test compound to the GPCR-like protein can be determined either directly or indirectly as described above. In a preferred embodiment, the assay includes contacting the GPCR-like protein or biologically active portion thereof with a known compound that binds GPCR-like protein to form an assay mixture, contacting the assay mixture with a test compound, and determining the ability of the test compound to preferentially bind to GPCR-like protein or biologically active portion thereof as compared to the known compound.

In another embodiment, an assay is a cell-free assay comprising contacting GPCR-like protein or biologically active portion thereof with a test compound and determining the ability of the test compound to modulate (e.g., stimulate or inhibit) the activity of the GPCR-like protein or biologically active portion thereof. Determining the ability of the test compound to modulate the activity of a GPCR-like protein can be accomplished, for example, by determining the ability of the GPCR-like protein to bind to a GPCR-like target molecule as described above for determining direct binding. In an alternative embodiment, determining the ability of the test compound to modulate the activity of a GPCR-like protein can be accomplished by determining the ability of the GPCR-like protein to further modulate a GPCR-like target molecule. For example, the catalytic/enzymatic activity of the target molecule on an appropriate substrate can be determined as previously described.

In yet another embodiment, the cell-free assay comprises contacting the GPCR-like protein or biologically active portion thereof with a known compound that binds a GPCR-like protein to form an assay mixture, contacting the assay mixture with a test compound, and determining the ability of the test compound to preferentially bind to or modulate the activity of a GPCR-like target molecule.

In the above-mentioned assays, it may be desirable to immobilize either a GPCR-like protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/GPCR-like fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or GPCR-like protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of GPCR-like binding or activity determined using standard techniques.

Other techniques for immobilizing proteins on matrices can also be used in the screening assays of the invention. For example, either GPCR-like protein or its target molecule can be immobilized utilizing conjugation of biotin and streptavidin. Biotinylated GPCR-like molecules or target molecules can be prepared from biotin-NHS (N-hydroxysuccinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a GPCR-like protein or target molecules but which do not interfere with binding of the GPCR-like protein to its target molecule can be derivatized to the wells of the plate, and unbound target or GPCR-like protein trapped in the wells by antibody conjugation. Methods for detecting such complexes, in addition to those described above for the GST-immobilized complexes, include immunodetection of complexes using antibodies reactive with the GPCR-like protein or target molecule, as well as enzyme-linked assays that rely on detecting an enzymatic activity associated with the GPCR-like protein or target molecule.

In another embodiment, modulators of GPCR-like expression are identified in a method in which a cell is contacted with a candidate compound and the expression of GPCR-like mRNA or protein in the cell is determined relative to expression of GPCR-like mRNA or protein in a cell in the absence of the candidate compound. When expression is greater (statistically significantly greater) in the presence of the candidate compound than in its absence, the candidate compound is identified as a stimulator of GPCR-like mRNA or protein expression. Alternatively, when expression is less (statistically significantly less) in the presence of the candidate compound than in its absence, the candidate compound is identified as an inhibitor of GPCR-like mRNA or protein expression. The level of GPCR-like mRNA or protein expression in the cells can be determined by methods described herein for detecting GPCR-like mRNA or protein.

In yet another aspect of the invention, the GPCR-like proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with GPCR-like protein ("GPCR-like-binding proteins" or "GPCR-like-bp") and modulate GPCR-like activity. Such GPCR-like-binding proteins are also likely to be involved in the propagation of signals by the GPCR-like proteins as, for example, upstream or downstream elements of the GPCR-like pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial GPCR-like gene sequences of the invention can be used to map their respective GPCR-like genes on a chromosome, thereby facilitating the location of gene regions associated with genetic disease. Computer analysis of GPCR-like sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the GPCR-like sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919–924). Somatic cell hybrids containing only fragments of human chromosomes can also be produced by using human chromosomes with translocations and deletions.

Other mapping strategies that can similarly be used to map a GPCR-like sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) *Human Chromosomes: A Manual ofBasic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Another strategy to map the chromosomal location of GPCR-like genes uses GPCR-like polypeptides and fragments and sequences of the present invention and antibodies specific thereto. This mapping can be carried out by specifically detecting the presence of a GPCR-like polypeptide in members of a panel of somatic cell hybrids between cells of a first species of animal from which the protein originates and cells from a second species of animal, and then determining which somatic cell hybrid(s) expresses on the polypeptide and noting the chromosomes(s) from the first species of animal that it contains. For examples of this technique, see Pajunen et al. (1988) *Cytogenet. Cell. Genet.* 47:37–41 and Van Keuren et al. (1986) *Hum. Genet.* 74:34–40. Alternatively, the presence of a GPCR-like polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the GPCR-like gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The GPCR-like sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described, e.g., in U.S. Pat. No. 5,272,057).

Furthermore, the sequences of the present invention can be used to provide an alternative technique for determining the actual base-by-base DNA sequence of selected portions of an individual's genome. Thus, the GPCR-like sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The GPCR-like sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:1 can comfortably provide positive individual identification with a panel of perhaps 10 to 1,000 primers that each yield a noncoding amplified sequence of 100 bases. If a predicted coding sequence, such as that in SEQ ID NO:2, is used, a more appropriate number of primers for positive individual identification would be 500 to 2,000.

3. Use of Partial GPCR-like Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Exanmples of polynucleotide reagents include the GPCR-like sequences or portions thereof, e.g., fragments derived from the noncoding regions of SEQ ID NO:1 having a length of at least 20 or 30 bases.

The GPCR-like sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such GPCR-like probes, can be used to identify tissue by species andior by organ type.

In a similar fashion, these reagents, e.g., GPCR-like primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting GPCR-like protein and/or nucleic acid expression as well as GPCR-like activity, in the context of a biological sample. An exemplary method for detecting the presence or absence of GPCR-like proteins in a biological sample involves obtaining a biological sample from a test subject and contacting the biological sample with a compound or an agent capable of detecting GPCR-like protein or nucleic acid (e.g., mRNA, genomic DNA) that encodes GPCR-like protein such that the presence of GPCR-like protein is detected in the biological sample. Results obtained with a biological sample from the test subject may be compared to results obtained with a biological sample from a control subject.

A preferred agent for detecting GPCR-like mRNA or genomic DNA is a labeled nucleic acid probe capable of hybridizing to GPCR-like mRNA or genomic DNA. The nucleic acid probe can be, for example, a full-length GPCR-like nucleic acid, such as the nucleic acid of SEQ ID NO:1, or a portion thereof, such as a nucleic acid molecule of at least 15, 30, 50, 100, 250, or 500 nucleotides in length and sufficient to specifically hybridize under stringent conditions to GPCR-like mRNA or genomic DNA. Other suitable probes for use in the diagnostic assays of the invention are described herein.

A preferred agent for detecting GPCR-like protein is an antibody capable of binding to GPCR-like protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect GPCR-like mRNA, protein, or genomic DNA in a biological sample in vitro as well as in vivo. For example, in vitro techniques for detection of GPCR-like mRNA include Northern hybridizations and in situ hybridizations. In vitro techniques for detection of GPCR-like protein include enzyme linked immunosorbent assays (ELISAs), Western blots, immunoprecipitations, and immunofluorescence. In vitro techniques for detection of GPCR-like genomic DNA include Southern hybridizations. Furthermore, in vivo techniques for detection of GPCR-like protein include introducing into a subject a labeled anti-GPCR-like antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject.

The invention also encompasses kits for detecting the presence of GPCR-like proteins in a biological sample (a test sample). Such kits can be used to determine if a subject is suffering from or is at increased risk of developing a disorder associated with aberrant expression of GPCR-like protein (e.g., a pain, central or peripheral nervous system, immune, inflammatory, endocrine or exocrine disorder). For example, the kit can comprise a labeled compound or agent capable of detecting GPCR-like protein or mRNA in a biological sample and means for determining the amount of a GPCR-like protein in the sample (e.g., an anti-GPCR-like antibody or an oligonucleotide probe that binds to DNA encoding a GPCR-like protein, e.g., SEQ ID NO:1). Kits can also include instructions for observing that the tested subject is suffering from or is at risk of developing a disorder associated with aberrant expression of GPCR-like sequences if the amount of GPCR-like protein or mRNA is above or below a normal level.

For antibody-based kits, the kit can comprise, for example: (1) a first antibody (e.g., attached to a solid support) that binds to GPCR-like protein; and, optionally, (2) a second, different antibody that binds to GPCR-like protein or the first antibody and is conjugated to a detectable agent. For oligonucleotide-based kits, the kit can comprise, for example: (1) an oligonucleotide, e.g., a detectably labeled oligonucleotide, that hybridizes to a GPCR-like nucleic acid sequence or (2) a pair of primers useful for amplifying a GPCR-like nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of GPCR-like proteins.

2. Other Diagnostic Assays

In another aspect, the invention features a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a GPCR-like nucleic acid, preferably purified, polypeptide, preferably purified, or antibody, and thereby evaluating the plurality of capture probes. Binding, e.g., in the case of a nucleic acid, hybridization, with a capture probe at an address of the plurality, is detected, e.g., by signal generated from a label attached to the GPCR-like nucleic acid, polypeptide, or antibody. The capture probes can be a set of nucleic acids from a selected sample, e.g., a sample of nucleic acids derived from a control or non-stimulated tissue or cell.

The method can include contacting the GPCR-like nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of a GPCR-like sequence of the invention. Such methods can be used to diagnose a subject, e.g., to evaluate risk for a disease or disorder, to evaluate suitability-of a selected treatment for a subject, to evaluate whether a subject has a disease or disorder. Thus, for example, the 43239 sequence set forth in SEQ ID NO:1 encodes a GPCR-like polypeptide that is associated with pain, thus it is useful for evaluating pain disorders.

The method can be used to detect single nucleotide polymorphisms (SNPs), as described below.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express a GPCR-like polypeptide of the invention or from a cell or subject in which a GPCR-like-mediated response has been elicited, e.g., by contact of the cell with a GPCR-like nucleic acid or protein of the invention, or administration to the cell or subject a GPCR-like nucleic acid or protein of the invention; contacting the array with one or more inquiry probes, wherein an inquiry probe can be a nucleic acid, polypeptide, or antibody (which is preferably other than a GPCR-like nucleic acid, polypeptide, or antibody of the invention); providing a two dimensional array having a plurality of addresses, each address of the plurality being positionally distinguishable from each other address of the plurality, and each address of the plurality having a unique capture probe, e.g., wherein the capture probes are from a cell or subject which does not express a GPCR-like sequence of the invention (or does not express as highly as in the case of the GPCR-like positive plurality of capture probes) or from a cell or subject in which a GPCR-like-mediated response has not been elicited (or has been elicited to a lesser extent than in the first sample); contacting the array with one or more inquiry probes (which is preferably other than a GPCR-like nucleic acid, polypeptide, or antibody of the invention), and thereby evaluating the plurality of capture probes. Binding, e.g., in the case of a nucleic acid, hybridization, with a capture probe at an address of the plurality, is detected, e.g., by signal generated from a label attached to the nucleic acid, polypeptide, or antibody.

In another aspect, the invention features a method of analyzing a GPCR-like sequence of the invention, e.g., analyzing structure, function, or relatedness to other nucleic acid or amino acid sequences. The method includes: providing a GPCR-like nucleic acid or amino acid sequence, e.g., the 43239 sequence set forth in SEQ ID NO:1 or a portion thereof; comparing the GPCR-like sequence with one or more preferably a plurality of sequences from a collection of sequences, e.g., a nucleic acid or protein sequence database; to thereby analyze the GPCR-like sequence of the invention.

The method can include evaluating the sequence identity between a GPCR-like sequence of the invention, e.g., the 43239 sequence, and a database sequence. The method can be performed by accessing the database at a second site, e.g., over the internet.

In another aspect, the invention features, a set of oligonucleotides, useful, e.g., for identifying SNP's, or identifying specific alleles of a GPCR-like sequence of the invention, e.g., the 43239 sequence. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

3. Prognostic Assays

The methods described herein can furthermore be utilized as diagnostic or prognostic assays to identify subjects having or at risk of developing a disease or disorder associated with GPCR-like protein, GPCR-like nucleic acid expression, or GPCR-like activity. Prognostic assays can be used for prognostic or predictive purposes to thereby prophylactically treat an individual prior to the onset of a disorder characterized by or associated with GPCR-like protein, GPCR-like nucleic acid expression, or GPCR-like activity.

Thus, the present invention provides a method in which a test sample is obtained from a subject, and GPCR-like protein or nucleic acid (e.g., mRNA, genomic DNA) is detected, wherein the presence of GPCR-like protein or nucleic acid is diagnostic for a subject having or at risk of developing a disease or disorder associated with aberrant GPCR-like expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease GPCR-like activity) to effectively treat a disease or disorder associated with aberrant GPCR-like expression or activity. In this manner, a test sample is obtained and GPCR-like protein or nucleic acid is detected. The presence of GPCR-like protein or nucleic acid is diagnostic for a subject that can be administered the agent to treat a disorder associated with aberrant GPCR-like expression or activity.

The methods of the invention can also be used to detect genetic lesions or mutations in a GPCR-like gene, thereby determining if a subject with the lesioned gene is at risk for a disorder characterized by aberrant pain transmissions, an aberrant immune or inflammatory response, aberrant cell growth, differentiation or death, aberrant nervous system development or function, or the aberrant release of hormones, neurotransmitters or cytokines. In preferred embodiments, the methods include detecting, in a sample of cells from the subject, the presence or absence of a genetic lesion or mutation characterized by at least one of an alteration affecting the integrity of a gene encoding a GPCR-like-protein, or the misexpression of the GPCR-like gene. For example, such genetic lesions or mutations can be detected by ascertaining the existence of at least one of: (1) a deletion of one or more nucleotides from a GPCR-like gene; (2) an addition of one or more nucleotides to a GPCR-like gene; (3) a substitution of one or more nucleotides of a GPCR-like gene; (4) a chromosomal rearrangement of a GPCR-like gene; (5) an alteration in the level of a messenger RNA transcript of a GPCR-like gene; (6) an aberrant modification of a GPCR-like gene, such as of the methylation pattern of the genomic DNA; (7) the presence of a non-wild-type splicing pattern of a messenger. RNA transcript of a GPCR-like gene; (8) a non-wild-type level of a GPCR-like-protein; (9) an allelic loss of a GPCR-like gene; and (10) an inappropriate post-translational modification of a GPCR-like-protein. As described herein, there are a large number of assay techniques known in the art that can be used for detecting lesions in a GPCR-like gene. Any cell type or tissue, for example a dorsal root ganrglion neuron, in which GPCR-like proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the GPCR-like-gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a GPCR-like gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a GPCR-like molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the GPCR-like gene and detect mutations by comparing the sequence of the sample GPCR-like gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin etal. (1993) *Appl. Biochem. Biotechnol.* 38:147–159).

Other methods for detecting mutations in the GPCR-like gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1 992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in GPCR-like cDNAs obtained from samples of cells. See, e.g., Hsu et al. (1994) *Carcinogenesis* 15:1657–1662. According to an exemplary embodiment, a probe based on a GPCR-like sequence, e.g., a wild-type GPCR-like sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in GPCR-like genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGEj (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such-cases, ligation will occur only if there is a perfect match at the 3' end of the 5' sequence making it possible to detect the presence of a known mutation at a specific site by looking for the presence or absence of amplification.

The methods described herein may be performned, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving a GPCR-like gene.

4. Pharmacogenomics

Agents, or modulators that have a stimulatory or inhibitory effect on GPCR-like activity (e.g., GPCR-like gene expression) as identified by a screening assay described herein, can be administered to individuals to treat (prophylactically or therapeutically) disorders associated with aberrant GPCR-like activity as well as to modulate the phenotype of a pain or neurologic disorder or an immune or inflammatory response. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of GPCR-like protein, expression of GPCR-like nucleic acid, or mutation content of GPCR-like genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, an "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a GPCR-like protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a GPCR-like molecule or GPCR-like modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a GPCR-like molecule or GPCR-like modulator of the invention, such as a modulator identified by one of the exemplary screening assays described herein.

The present invention further provides methods for identifying new agents, or combinations, that are based on identifying agents that modulate the activity of one or more of the gene products encoded by one or more of the GPCR-like genes of the present invention, wherein these products may be associated with resistance of the cells to a therapeutic agent. Specifically, the activity of the proteins encoded by the GPCR-like genes of the present invention can be used as a basis for identifying agents for overcoming agent resistance. By blocking the activity of one or more of the resistance proteins, target cells, e.g., DRG cells, will become sensitive to treatment with an agent that the unmodified target cells were resistant to.

Monitoring the influence of agents (e.g., drugs) on the expression or activity of a GPCR-like protein can be applied in clinical trials. For example, the effectiveness of an agent determined by a screening assay as described herein to increase GPCR-like gene expression, protein levels, or upregulate GPCR-like activity, can be monitored in clinical trials of subjects exhibiting decreased GPCR-like gene expression, protein levels, or downregulated GPCR-like activity. Alternatively, the effectiveness of an agent determined by a screening assay to decrease GPCR-like gene expression, protein levels, or downregulate GPCR-like activity, can be monitored in clinical trials of subjects exhibiting-increased GPCR-like gene expression, protein levels, or upregulated GPCR-like activity. In such clinical trials, the expression or activity of a GPCR-like gene, and preferably, other genes that have been implicated in, for example, a GPCR-like-associated disorder can be used as a "read out" or markers of the phenotype of a particular cell.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of GPCR-like protein, expression of GPCR-like nucleic acid, or mutation content of GPCR-like genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a GPCR-like modulator, such as a modulator identified by one of the exemplary screening assays described herein.

5. Monitoring of Effects During Clinical Trials

Monitoring the influence of agents (e.g., drugs, compounds) on the expression or activity of GPCR-like genes (e.g., the ability to modulate aberrant pain transmission, nervous system development and function, immune and inflammatory responses, cell growth, differentiation, and death, and the release of neurotransmitters, hormones, and cytokines) can be applied not only in basic drug screening but also in clinical trials. For example, the effectiveness of an agent, as determined by a screening assay as described herein, to increase or decrease GPCR-like gene expression, protein levels, or protein activity, can be monitored in clinical trials of subjects exhibiting decreased or increased GPCR-like gene expression, protein levels, or protein activity. In such clinical trials, GPCR-like expression or activity and preferably that of other genes that have been implicated in for example, pain, neurologic, immune or inflammatory disorders, can be used as a marker of the responsiveness of a particular cell.

For example, and not by way of limitation, genes that are modulated in cells by treatment with an agent (e.g., compound, drug, or small molecule) that modulates GPCR-like activity (e.g., as identified in a screening assay described herein) can be identified. Thus, to study the effect of agents on pain, neurologic, exocrine, endocrine, inflammatory and immune disorders, for example, in a clinical trial, cells can be isolated and RNA prepared and analyzed for the levels of expression of GPCR-like genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of GPCR-like genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a GPCR-like protein, mRNA, or genomic DNA in the preadministration sample; (3) obtaining one or more post-administration samples from the subject; (4) detecting the level of expression or activity of the GPCR-like protein, mRNA, or genomic DNA in the postadministration samples; (5) comparing the level of expression or activity of the GPCR-like protein, mRNA, or genomic DNA in the preadministration sample with the GPCR-like protein, mRNA, or genomic DNA in the postadministration sample or samples; and (vi) altering the administration of the agent to the subject accordingly to bring about the desired effect, i.e., for example, an increase or a decrease in the expression or activity of a GPCR-like protein.

C. Methods of Treatment

The present invention provides for both prophylactic and therapeutic methods of treating a subject at risk of (or susceptible to) a disorder or having a disorder associated with aberrant GPCR-like expression or activity. Additionally, the compositions of the invention find use in the treatment of disorders described herein. Thus, therapies for disorders associated with aberrant GPCR-like expression or activity are encompassed herein.

1. Prophylactic Methods

In one aspect, the invention provides a method for preventing in a subject a disease or condition associated with an aberrant GPCR-like expression or activity by administering to the subject an agent that modulates GPCR-like expression or at least one GPCR-like gene activity. Subjects at risk for a disease that is caused, or contributed to, by aberrant GPCR-like expression or activity can be identified by, for example, any or a combination of diagnostic or prognostic assays as described herein. Administration of a prophylactic agent can occur prior to the manifestation of symptoms characteristic of the GPCR-like aberrancy, such that a disease or disorder is prevented or, alternatively, delayed in its progression. Depending on the type of GPCR-like aberrancy, for example, a GPCR-like agonist or GPCR-like antagonist agent can be used for treating the subject. The appropriate agent can be determined based on screening assays described herein.

2. Therapeutic Methods

Another aspect of the invention pertains to methods of modulating GPCR-like expression or activity for therapeutic purposes. The modulatory method of the invention involves contacting a cell with an agent that modulates one or more of the activities of GPCR-like protein activity associated with the cell. An agent that modulates GPCR-like protein activity can be an agent as described herein, such as a nucleic acid or a protein, a naturally-occurring cognate ligand of a GPCR-like protein, a peptide, a GPCR-like peptidomimetic, or other small molecule. In one embodiment, the agent stimulates one or more of the biological activities of GPCR-like protein. Examples of such stimulatory agents include active GPCR-like protein and a nucleic acid molecule encoding a GPCR-like protein that has been introduced into the cell. In another embodiment, the agent inhibits one or more of the biological activities of GPCR-like protein. Examples of such inhibitory agents include antisense GPCR-like nucleic acid molecules and anti-GPCR-like antibodies.

These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a GPCR-like protein or nucleic acid molecule. In one embodiment, the method involves administering an agent (e.g., an agent identified by a screening assay described herein), or a combination of agents, that modulates (e.g., upregulates or downregulates) GPCR-like expression or activity. In another embodiment, the method involves administering a GPCR-like protein or nucleic acid molecule as therapy to compensate for reduced or aberrant GPCR-like expression or activity.

Stimulation of GPCR-like activity is desirable in situations in which a GPCR-like protein is abnormally downregulated and/or in which increased GPCR-like activity is likely to have a beneficial effect. Conversely, inhibition of GPCR-like activity is desirable in situations in which GPCR-like activity is abnormally upregulated and/or in which decreased GPCR-like activity is likely to have a beneficial effect.

This invention is further illustrated by the following examples, which should not be construed as limiting.

EXPERIMENTAL

Example 1 mRNA Expression of Clone 43239

Taqman analysis of 43239 revealed expression in a number of human tissues (FIG. 1). Low levels of expression are seen in kidney, liver, lung, and skin. Moderate expression levels are seen in tissue from the spinal cord, heart, and brain. The highest level of 43239 mRNA expression was in human dorsal root ganglion neurons (DRG).

Figure 2:
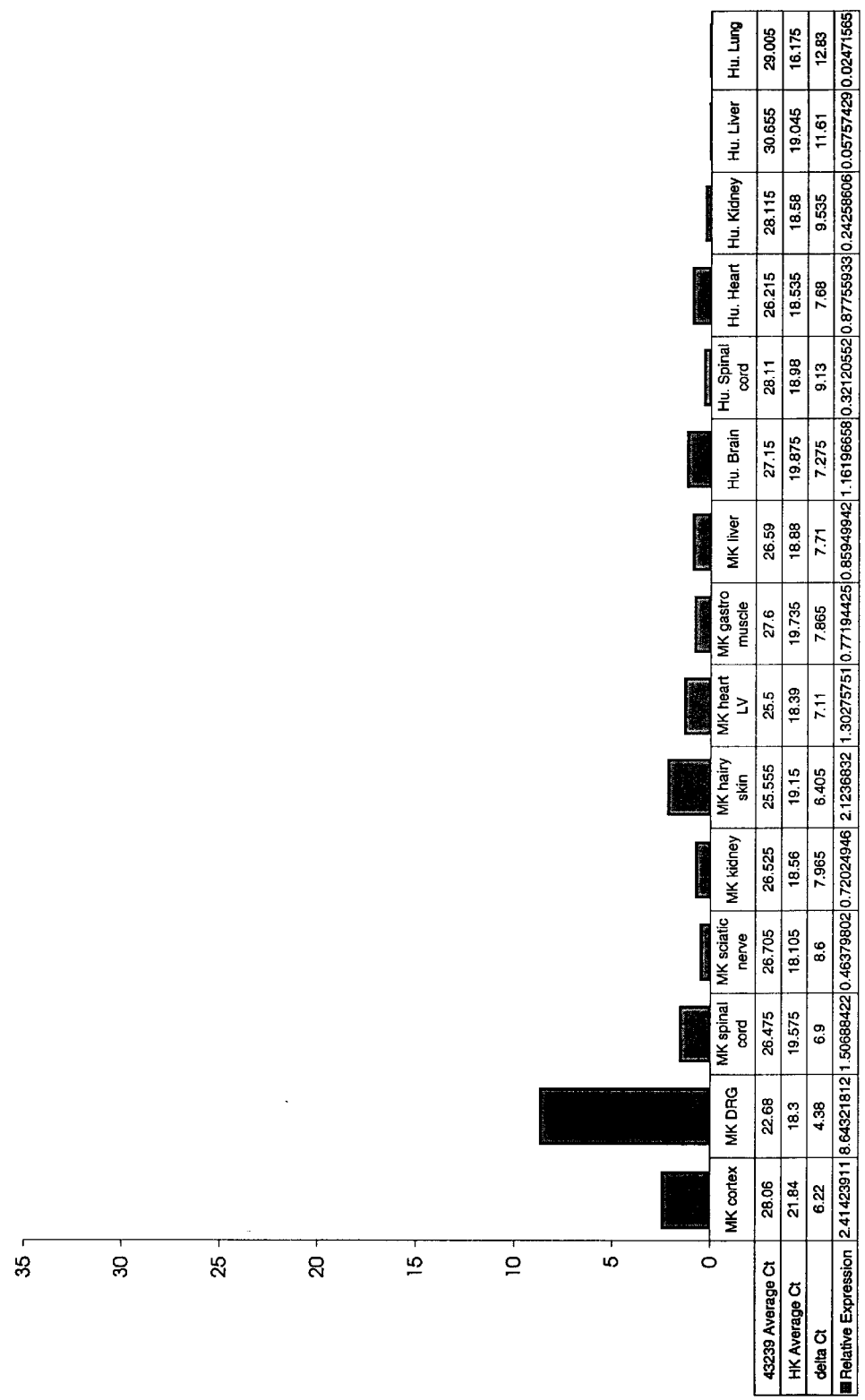
FIG. 2 shows expression of 43239 in various monkey and human tissues and cell types.

FIG. 2 shows the 43239 mRNA is expressed in various tissues and cells from monkey. Moderate levels of 43239 expression were detected in monkey cortex, spinal cord, sciatic nerve, kidney, hairy skin, heart, gastro muscle and liver. The highest level of 43239 expression in monkey tissue was found in the dorsal root ganglion neurons. The expression of 43239 mRNA in the dorsal root ganglion neurons was verified by in situ hybridization (data not shown).

All publications and patent applications mentioned in the specification are indicative of the level of those skilled in the art to which this invention pertains. All publications and patent applications are herein incorporated by reference to the sarne extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

---

What is claimed is:

1. An isolated nucleic acid molecule selected from the group consisting of:
   a) a nucleic acid molecule comprising the nucleotide sequence of SEQ ID NO:1, the cDNA insert of the plasmids deposited with the ATCC as Accession Numbers PTA-2365, PTA-2166, or PTA-2366, or a complement thereof; and
   b) a nucleic acid molecule which encodes a polypeptide comprising the amino acid sequence of SEQ ID NO:2, or an amino acid sequence encoded by the cDNA insert of the plasmids deposited with the ATCC as Accession Numbers PTA-2365, PTA-2166, or PTA-2366.

2. The isolated nucleic acid molecule of claim 1 further comprising vector nucleic acid sequences.

3. The isolated nucleic acid molecule of claim 1 further comprising nucleic acid sequences encoding a heterologous polypeptide.

4. A host cell which contains the isolated nucleic acid molecule of claim 2.

5. The host cell of claim 4 which is a mammalian host cell.

6. A non-human mammalian host cell containing the isolated nucleic acid molecule of claim 1.

7. A method for producing a polypeptide comprising culturing the host cell of claim 4 under conditions in which the nucleic acid molecule is expressed.

8. A method for modulating the level of a polypeptide comprising expressing an isolated nucleic acid molecule of claim 1 in a transformed host cell.

* * * * *

SEQUENCE LISTING

<160> NUMBER OF SEQ ID NOS: 2

<210> SEQ ID NO 1
<211> LENGTH: 1401
<212> TYPE: DNA
<213> ORGANISM: Homo sapiens
<220> FEATURE:
<221> NAME/KEY: CDS
<222> LOCATION: (197)...(1237)

<400> SEQUENCE: 1
cgaattcggc ttggaaagct ggtacgcctg caggtaccgg tccggaattc ccgggtcgac      60

-continued

```
ccacgcgtcc gagctgaaag acagagacct tcagggaaaa ctaggttcca agatggctga      120
ataggaagag ctccaatctg cagatcccag tgtgagcaac gtggaagacg ggtgatttct      180
gcatttccaa ctgagc atg gag aga aaa ttt atg tcc ttg caa cca tcc atc     232
              Met Glu Arg Lys Phe Met Ser Leu Gln Pro Ser Ile
               1               5                  10 tcc gta tca gaa atg gaa cca aat ggc acc ttc agc aat aac aac agc       280
Ser Val Ser Glu Met Glu Pro Asn Gly Thr Phe Ser Asn Asn Asn Ser
        15              20                  25 agg aac tgc aca att gaa aac ttc aag aga gaa ttt ttc cca att gta       328
Arg Asn Cys Thr Ile Glu Asn Phe Lys Arg Glu Phe Phe Pro Ile Val
 30                  35                  40 tat ctg ata ata ttt ttc tgg gga gtc ttg gga aat ggg ttg tcc ata       376
Tyr Leu Ile Ile Phe Phe Trp Gly Val Leu Gly Asn Gly Leu Ser Ile
 45                  50                  55                  60 tat gtt ttc ctg cag cct tat aag aag tcc aca tct gtg aac gtt ttc       424
Tyr Val Phe Leu Gln Pro Tyr Lys Lys Ser Thr Ser Val Asn Val Phe
                 65                  70                  75 atg cta aat ctg gcc att tca gat ctc ctg ttc ata agc acg ctt ccc       472
Met Leu Asn Leu Ala Ile Ser Asp Leu Leu Phe Ile Ser Thr Leu Pro
         80                  85                  90 ttc agg gct gac tat tat ctt aga ggc tcc agt tgg ata ttt gga gac       520
Phe Arg Ala Asp Tyr Tyr Leu Arg Gly Ser Ser Trp Ile Phe Gly Asp
     95                 100                 105 ctg gcc tgc agg att atg tct tat tcc ttg tat gtc aac atg tac agc       568
Leu Ala Cys Arg Ile Met Ser Tyr Ser Leu Tyr Val Asn Met Tyr Ser
110                 115                 120 agt att tat ttc ctg acc gtg ctg agt gtt gtg cgt ttc ctg gca atg       616
Ser Ile Tyr Phe Leu Thr Val Leu Ser Val Val Arg Phe Leu Ala Met
125                 130                 135                 140 gtt cac ccc ttt cgg ctt ctg cat gtc acc agc atc agg agt gcc tgg       664
Val His Pro Phe Arg Leu Leu His Val Thr Ser Ile Arg Ser Ala Trp
                145                 150                 155 atc ctc tgt ggg atc ata tgg atc ctt atc atg gct tcc tca ata atg       712
Ile Leu Cys Gly Ile Ile Trp Ile Leu Ile Met Ala Ser Ser Ile Met
            160                 165                 170 ctc ctg gac agt ggc tct gag cag aac ggc agt gtc aca tca tgc tta       760
Leu Leu Asp Ser Gly Ser Glu Gln Asn Gly Ser Val Thr Ser Cys Leu
        175                 180                 185 gag ctg aat ctc tat aaa att gct aag ctg cag acc atg aac tat att       808
Glu Leu Asn Leu Tyr Lys Ile Ala Lys Leu Gln Thr Met Asn Tyr Ile
    190                 195                 200 gcc ttg gtg gtg ggc tgc ctg ctg cca ttt ttc aca ctc agc atc tgt       856
Ala Leu Val Val Gly Cys Leu Leu Pro Phe Phe Thr Leu Ser Ile Cys
205                 210                 215                 220 tat ctg ctg atc att cgg gtt ctg tta aaa gtg gag gtc cca gaa tcg       904
Tyr Leu Leu Ile Ile Arg Val Leu Leu Lys Val Glu Val Pro Glu Ser
                225                 230                 235 ggg ctg cgg gtt tct cac agg aag gca ctg acc acc atc atc atc acc       952
Gly Leu Arg Val Ser His Arg Lys Ala Leu Thr Thr Ile Ile Ile Thr
            240                 245                 250 ttg atc atc ttc ttc ttg tgt ttc ctg ccc tat cac aca ctg agg acc      1000
Leu Ile Ile Phe Phe Leu Cys Phe Leu Pro Tyr His Thr Leu Arg Thr
        255                 260                 265 gtc cac ttg acg aca tgg aaa gtg ggt tta tgc aaa gac aga ctg cat      1048
Val His Leu Thr Thr Trp Lys Val Gly Leu Cys Lys Asp Arg Leu His
    270                 275                 280 aaa gct ttg gtt atc aca ctg gtc ttg gca gca gcc aat gcc tgc ttc      1096
Lys Ala Leu Val Ile Thr Leu Val Leu Ala Ala Ala Asn Ala Cys Phe
285                 290                 295                 300
```

-continued

```
aat cct ctg ctc tat tac ttt gct ggg gag aat ttt aag gac aga cta      1144
Asn Pro Leu Leu Tyr Tyr Phe Ala Gly Glu Asn Phe Lys Asp Arg Leu
            305                 310                 315 aag tct gca ctc aga aaa ggc cat cca cag aag gca aag aca aag tgt      1192
Lys Ser Ala Leu Arg Lys Gly His Pro Gln Lys Ala Lys Thr Lys Cys
        320                 325                 330 gtt ttc cct gtt agt gtg tgg ttg aga aag gaa aca aga gta taa          1237
Val Phe Pro Val Ser Val Trp Leu Arg Lys Glu Thr Arg Val
    335                 340                 345 ggagctctta gatgagacct gttcttgtat ccttgtgtcc atcttcgttc actcatagtc    1297
tccaaatgac tttgtattta catcactccc aacaaatgtt gattcttaat atttagttga    1357
ccattacttt tgktaataag acctacttca acttttgctt ttta                     1401

<210> SEQ ID NO 2
<211> LENGTH: 346
<212> TYPE: PRT
<213> ORGANISM: Homo sapiens

<400> SEQUENCE: 2

Met Glu Arg Lys Phe Met Ser Leu Gln Pro Ser Ile Ser Val Ser Glu
  1               5                  10                  15

Met Glu Pro Asn Gly Thr Phe Ser Asn Asn Ser Arg Asn Cys Thr
             20                  25                  30

Ile Glu Asn Phe Lys Arg Glu Phe Phe Pro Ile Val Tyr Leu Ile Ile
         35                  40                  45

Phe Phe Trp Gly Val Leu Gly Asn Gly Leu Ser Ile Tyr Val Phe Leu
     50                  55                  60

Gln Pro Tyr Lys Lys Ser Thr Ser Val Asn Val Phe Met Leu Asn Leu
65                  70                  75                  80

Ala Ile Ser Asp Leu Leu Phe Ile Ser Thr Leu Pro Phe Arg Ala Asp
                 85                  90                  95

Tyr Tyr Leu Arg Gly Ser Ser Trp Ile Phe Gly Asp Leu Ala Cys Arg
            100                 105                 110

Ile Met Ser Tyr Ser Leu Tyr Val Asn Met Tyr Ser Ser Ile Tyr Phe
        115                 120                 125

Leu Thr Val Leu Ser Val Val Arg Phe Leu Ala Met Val His Pro Phe
    130                 135                 140

Arg Leu Leu His Val Thr Ser Ile Arg Ser Ala Trp Ile Leu Cys Gly
145                 150                 155                 160

Ile Ile Trp Ile Leu Ile Met Ala Ser Ser Ile Met Leu Leu Asp Ser
                165                 170                 175

Gly Ser Glu Gln Asn Gly Ser Val Thr Ser Cys Leu Glu Leu Asn Leu
            180                 185                 190

Tyr Lys Ile Ala Lys Leu Gln Thr Met Asn Tyr Ile Ala Leu Val Val
        195                 200                 205

Gly Cys Leu Leu Pro Phe Phe Thr Leu Ser Ile Cys Tyr Leu Leu Ile
    210                 215                 220

Ile Arg Val Leu Leu Lys Val Glu Val Pro Glu Ser Gly Leu Arg Val
225                 230                 235                 240

Ser His Arg Lys Ala Leu Thr Thr Ile Ile Thr Leu Ile Ile Phe
                245                 250                 255

Phe Leu Cys Phe Leu Pro Tyr His Thr Leu Arg Thr Val His Leu Thr
            260                 265                 270

Thr Trp Lys Val Gly Leu Cys Lys Asp Arg Leu His Lys Ala Leu Val
```

-continued

```
              275                 280                 285
Ile Thr Leu Val Leu Ala Ala Ala Asn Ala Cys Phe Asn Pro Leu Leu
    290                 295                 300

Tyr Tyr Phe Ala Gly Glu Asn Phe Lys Asp Arg Leu Lys Ser Ala Leu
305                 310                 315                 320

Arg Lys Gly His Pro Gln Lys Ala Lys Thr Lys Cys Val Phe Pro Val
                325                 330                 335

Ser Val Trp Leu Arg Lys Glu Thr Arg Val
            340                 345
```